(12) United States Patent
Tu et al.

(10) Patent No.: US 7,094,225 B2
(45) Date of Patent: Aug. 22, 2006

(54) MEDICAL DEVICE AND METHODS OF USE OF GLAUCOMA TREATMENT

(75) Inventors: Hosheng Tu, Newport Coast, CA (US); Gregory T. Smedley, Irvine, CA (US); Barbara A. Niksch, Laguna Niguel, CA (US); David S. Haffner, Mission Viejo, CA (US)

(73) Assignee: Glaukos Corporation, Laguna Hills, CA (US)

( * ) Notice: Subject to any disclaimer, the term of this patent is extended or adjusted under 35 U.S.C. 154(b) by 530 days.

(21) Appl. No.: 10/139,800

(22) Filed: May 3, 2002

(65) Prior Publication Data

US 2002/0169130 A1 Nov. 14, 2002

Related U.S. Application Data

(60) Provisional application No. 60/288,325, filed on May 3, 2001.

(51) Int. Cl.
*A61M 35/00* (2006.01)

(52) U.S. Cl. ...................................................... 604/290
(58) Field of Classification Search .................. 604/19, 604/48, 73, 93.01, 128, 264, 289, 294, 297, 604/290; 606/107, 162

See application file for complete search history.

(56) References Cited

U.S. PATENT DOCUMENTS

| | | | |
|---|---|---|---|
| 3,788,327 A | 1/1974 | Donowitz et al. | |
| 4,037,604 A | 7/1977 | Newkirk | |
| 4,168,697 A | 9/1979 | Cantekin | |
| 4,175,563 A | 11/1979 | Arenberg et al. | |
| 4,402,681 A | 9/1983 | Haas et al. | |
| 4,428,746 A | 1/1984 | Mendez | |
| 4,468,216 A | * | 8/1984 | Muto ........................... 604/43 |

(Continued)

FOREIGN PATENT DOCUMENTS

| | | |
|---|---|---|
| AU | 200072059 A1 | 12/2000 |
| AU | 200072059 A1 | 7/2001 |
| EP | 0 898 947 A2 | 3/1999 |
| EP | 0 898 947 A3 | 3/1999 |
| EP | 0898 947 A2 | 3/1999 |
| EP | 1 114 27 A1 | 11/2001 |
| EP | 1 114 627 A1 | 11/2001 |
| WO | WO 89/00869 | 2/1989 |
| WO | WO 92/19294 | 11/1992 |
| WO | WO 94/13234 | 6/1994 |
| WO | WO 98/30181 | 7/1998 |
| WO | WO 99/26567 | 6/1999 |
| WO | WO 99/30641 | 6/1999 |
| WO | WO 00/64389 | 11/2000 |
| WO | WO 00/64390 | 11/2000 |
| WO | WO 00/64391 | 11/2000 |
| WO | WO 00/64393 | 11/2000 |
| WO | WO 00/72788 | 12/2000 |
| WO | WO 01/50943 | 7/2001 |
| WO | WO 01/78631 | 10/2001 |
| WO | WO 03/015659 A2 | 2/2003 |

OTHER PUBLICATIONS

Phillip C. Jacobi, MD, Thomas S. Dietlein, MD and Gunter k. Krieglstein, MD, *Goniocurettage for Removing Trabecular Meshwork: Clinical Results of a new Surgical Technique in Advanced Chronic Open–Angle Glaucoma*, American Journal of Ophthalmology, May 1999, pp. 505–510.

(Continued)

*Primary Examiner*—Manuel Mendez
(74) *Attorney, Agent, or Firm*—Knobbe Martens Olson & Bear LLP

(57) ABSTRACT

The invention relates generally medical devices and methods for the treatment of glaucoma in an animal eye and, more particularly, to medical devices and methods for treating tissue of the trabecular meshwork and/or Schlemm's canal of the eye to restore or rejuvenate a portion or all of the normal physiological function of directing aqueous outflow for maintaining a normal intraocular pressure in the eye.

23 Claims, 18 Drawing Sheets

U.S. PATENT DOCUMENTS

| | | | |
|---|---|---|---|
| 4,501,274 A | 2/1985 | Skjaerpe | |
| 4,521,210 A | 6/1985 | Wong | |
| 4,554,918 A | 11/1985 | White | |
| 4,604,087 A | 8/1986 | Joseph | |
| 4,632,842 A | 12/1986 | Karwoski et al. | |
| 4,634,418 A | 1/1987 | Binder | |
| 4,718,907 A | 1/1988 | Karwoski et al. | |
| 4,722,724 A | 2/1988 | Schocket | |
| 4,733,665 A | 3/1988 | Palmaz | |
| 4,750,901 A | 6/1988 | Moltena | |
| 4,846,172 A * | 7/1989 | Berlin | 606/4 |
| 4,870,953 A * | 10/1989 | DonMicheal et al. | 606/128 |
| 4,886,488 A | 12/1989 | White | |
| 4,900,300 A | 2/1990 | Lee | |
| 4,936,825 A | 6/1990 | Ungerleider | |
| 4,946,436 A | 8/1990 | Smith | |
| 4,968,296 A | 11/1990 | Ritch et al. | |
| 5,041,081 A | 8/1991 | Odrich | |
| 5,092,837 A | 3/1992 | Ritch et al. | |
| 5,129,895 A | 7/1992 | Vassiliadis et al. | |
| 5,171,213 A | 12/1992 | Price, Jr. | |
| 5,178,604 A | 1/1993 | Baerveldt et al. | |
| 5,180,362 A | 1/1993 | Worst | |
| 5,246,451 A | 9/1993 | Trescony et al. | |
| 5,300,020 A | 4/1994 | L'Esperance, Jr. | |
| 5,338,291 A | 8/1994 | Speckman et al. | |
| 5,346,464 A | 9/1994 | Camras | |
| 5,360,399 A | 11/1994 | Stegmann | |
| 5,370,607 A | 12/1994 | Memmen | |
| 5,370,641 A | 12/1994 | O'Donnell, Jr. | |
| 5,372,577 A | 12/1994 | Ungerleider | |
| 5,397,300 A | 3/1995 | Baerveldt et al. | |
| 5,433,701 A | 7/1995 | Rubinstein | |
| 5,454,796 A | 10/1995 | Krupin | |
| 5,472,440 A | 12/1995 | Beckman | |
| 5,476,445 A | 12/1995 | Baerveldt et al. | |
| 5,486,165 A | 1/1996 | Stegmann | |
| 5,520,631 A | 5/1996 | Nordquist et al. | |
| 5,558,629 A | 9/1996 | Baerveldt et al. | |
| 5,558,630 A | 9/1996 | Fisher | |
| 5,562,641 A | 10/1996 | Flomenblit et al. | |
| RE35,390 E | 12/1996 | Smith | |
| 5,601,094 A | 2/1997 | Reiss | |
| 5,626,558 A | 5/1997 | Suson | |
| 5,626,559 A | 5/1997 | Solomon | |
| 5,639,278 A | 6/1997 | Dereume et al. | |
| 5,676,679 A | 10/1997 | Simon et al. | |
| 5,702,419 A | 12/1997 | Berry et al. | |
| 5,704,907 A | 1/1998 | Nordquist et al. | |
| 5,741,333 A | 4/1998 | Frid | |
| 5,743,868 A | 4/1998 | Brown et al. | |
| 5,752,928 A | 5/1998 | de Roulhac et al. | |
| 5,807,302 A | 9/1998 | Wandel | |
| 5,810,870 A | 9/1998 | Myers et al. | |
| 5,830,139 A | 11/1998 | Abreu | |
| 5,865,831 A | 2/1999 | Cozean et al. | |
| 5,868,697 A | 2/1999 | Richter et al. | |
| 5,879,319 A | 3/1999 | Pynson et al. | |
| 5,882,327 A | 3/1999 | Jacob | |
| 5,893,837 A | 4/1999 | Eagles et al. | |
| 5,968,058 A | 10/1999 | Richter et al. | |
| 5,984,913 A * | 11/1999 | Kritzinger et al. | 604/541 |
| 6,004,302 A | 12/1999 | Brierley | |
| 6,007,510 A | 12/1999 | Nigam | |
| 6,007,511 A | 12/1999 | Prywes | |
| 6,045,557 A | 4/2000 | White et al. | |
| 6,050,970 A | 4/2000 | Baerveldt | |
| 6,059,812 A | 5/2000 | Clerc et al. | |
| 6,071,286 A | 6/2000 | Mawad | |
| 6,174,305 B1 | 1/2001 | Mikus et al. | |
| 6,194,415 B1 * | 2/2001 | Wheeler et al. | 514/250 |
| 6,231,597 B1 | 5/2001 | Deem et al. | |
| 6,241,721 B1 | 6/2001 | Cozean et al. | |
| 6,375,642 B1 | 4/2002 | Grieshaber et al. | |
| 6,450,984 B1 | 9/2002 | Lynch et al. | |
| 6,464,724 B1 | 10/2002 | Lynch et al. | |
| 6,533,768 B1 | 3/2003 | Hill | |
| 6,544,249 B1 | 4/2003 | Yu et al. | |
| 6,696,415 B1 * | 2/2004 | Gendron et al. | 514/12 |
| 2002/0013546 A1 | 1/2002 | Grieshaber et al. | |
| 2002/0026200 A1 | 2/2002 | Savage | |
| 2002/0072673 A1 | 6/2002 | Yamamoto et al. | |
| 2003/0069637 A1 | 4/2003 | Lynch et al. | |

OTHER PUBLICATIONS

Phillip C. Jacobi, MD, Thomas S. Dietlein, MD and Gunter K. Krieglstein, MD, *Bimanual Trabecular Aspiration in Pseudoexfoliation Glaucoma*, Ophthalmology, 1998, vol. 105, No. 5, May 1998, pp. 886–894.

Phillip C. Jacobi, MD, Thomas S. Dietlein, MD and Gunter K. Krieglstein, MD, *Microendoscopic Trabecular Surgery in Glaucoma Management*, Opthamology, 199 vol. 106, No. 3, pp. 538–544.

Arthur L. Schwartz, MD, & Douglas R. Anderson, MD, *Trabecular Surgery*, Arch Opthalmol. vol. 92, Aug. 1974. pp. 134–138.

R.A. Hill, Q. Ren, D.C. Nguyen, L.H. Liaw, & M.W. Berns, *Free–election Laser (FEL) Ablation of Ocular Tissues*, Laser Med Sci 1998, vol. 13, pp. 219–226.

Maurice H. Luntz, MD & D.G. Livingston, B.SC., *Trabeculotomy AB Externo & Trabeculectomy in Congenital and Adult–Onset Glaucoma*, American Journal of Ophthalmology, Feb. 1977, vol. 83, No. 2, pp. 174–179.

W.M. Grant, MD, *Further Studies on Facility of Flow Through the Trabecular Meshwork*, AMA Archives of Ophthalmology, Oct. 1958, vol. 60, pp. 523–533.

Detliev Spiegel, MD, Karin Kobuch, MD, Richard A. Hill, MD, Ronald, L.Gross, *Schlemm's Canal Implant: A New Method to Lower Intraocular Pressure in Patients With POAG*, Opthalmic Surgery and Lasers, Jun. 1999, vol. 30, No. 6, pp. 492–494.

Copending U.S. Appl. No. of Dr. Richard Hill, U.S. Appl. No. 09/549,349, filed on Apr. 14, 2000, entitled *Device for Glaucoma Treatment and Methods Thereof*.

L. Jay Katz, MD., *A Call for Innovative Operations for Glaucoma*, Arch Ophthalmology, Mar. 2000, vol. 118, pp. 412–413.

Anselm Kampik & Franz Grehn, *Nutzen und Risiken Augenärzticher Therapie, Hauptreferate der XXXIII, Essener Fortbildung für Augenärzte*, Dec. 1998. (English translated version enclosed Benefits and Risks of Ophthalmological Therapy).

Detlev Spiegel, *7 Chirurgische Glaukomtherapie*, pp. 79–88 (English translation enclosed).

U.S. Appl. No. 09/452,963, filed Dec. 2, 1999, Inventor: Hosheng Tu, entitled: *Expandable/Retractable Stent For Venous And Valvular Annulus Use*.

Sunita Radhakrishnan, Andrew M. Rollins, Jonathan E. Roth, S. Yazdanfar, Volker Westphal, David Bardenstein & Joseph Izatt, *Real–time Optical Conherence Tomography of the Anterior Segment at 1310 MM*, Arch Ophthalmology, Aug. 2001, vol. 119, pp. 1179–1185.

Hans Hoerauf, Christopher Wirbelauer, Christian Scholz, Ralf Engelhardt, peter Koch, Horst Iagua, and Reginald Bimgruber, *Slit–Lamp–AdaptedOoptical Coherence Tomography of the Anterior Segment*, Graefe's Arch Clin. Exp Ophthalmol, May 1999, vol. 238, pp. 8–18.

Phillip C. Jacobi, MD, Thomas S. Dietlein, MD and Gunter K. Krieglstein, MD, *Goniocurettage for Removing Trabecular Meshwork: Clinical Results of a new Surgical Technique in Advanced Cronic Open–Angle Glaucoma*, American Journal of Ophthalmology, May 1999, pp. 505–510.

Phillip C. Jacobi, MD, Thomas S. Dietlein, MD and Gunter K. Krieglstein, MD, *Bimanual Trabecular Aspiration in Pseudoexfoliation Glaucoma*, Ophthalmology, 1998, vol 105, No. 5, May 1998, pp. 886–894.

Phillip C. Jacobi, MD, Thomas S. Dietlein, MD and Gunter K. Krieglstein, MD, *Microendoscopic Trabecular Surgery in Glaucoma Management*, Ophthalmology, 1999 vol. 106, No. 3, pp. 538–544.

Arthur L. Schwartz, MD, & Douglas R. Anderson, MD, *Trabecular Surgery*, Arch Ophthalmol, vol. 92, Aug. 1974, pp. 134–138.

R.A. Hill, Q. Ren, D.C. Nguyen, L.H. Liaw, & M.W. Bems, *Free–election Laser (FEL) Ablation of Ocular Tissues*, Laser Med Sci 1998, vol. 13, pp. 219–226.

Maurice H. Luntz, MD & D.G. Livingston, B.SC., *Trabeculotomy AB Extern & Trabeculectomy in Congenital and Adult–Onset Glaucoma*, American Journal of Ophthalmology, Feb. 1977, vol. 83, No. 2, pp. 174–179.

W.M. Grant, MD, *Further Studies on Facility of Flow Through the Trabecular Meshwork*, AMA Archives of Ophthalmology, Oct. 1958, vol. 60, pp. 523–533.

Richard A. Hill, MD, George Baerveldt, MD, Serdar A. Ozler, MD, Michael Pickford, BA, Glen A, Profeta, BS & Michael W. Bems, PhD, *Laser Trabecular Ablation (LTA)*, Laser in Surgery and Medicine, 1991, vol. 11, pp. 341–346.

Detliev Spiegel, MD, Karin Kobuch, MD, Richard A. Hill, MD, Ronald L. Gross, MD, *Schlemm's Canal Implant: A New Method to Lower Intraocular Pressure in Patients With POAG*, Ophthalmic Surgery and Lasers, Jun. 1999, vol. 30, No. 6, pp. 492–494.

Copending U.S. Patent Application of Dr. Richard Hill, U.S. Appl. No. 09/549,349, filed on Apr. 14, 2000, entitled *Device for Glaucoma Treatment and Methods Thereof*.

L. Jay Katz, MD., *A Call for Innovative Operation for Glaucoma*, Arch Ophthalmology, Mar. 2000, vol. 118, pp. 412–413.

Anselm Kampik & Franz Grehn, *Nutzen and Risiken Augenärzticher Therapie, Hauptreferate der XXXIII, Essner Forbildung für Augenärzte*, Dec. 1998. (English translated version enclosed Benefits and Risks of Ophthalmological Therapy).

Detlev Spiegel, *7 Chirurgische Glaukomtherapie*, pp. 79–88 (English translation enclosed).

U.S. Appl. No. 09/452,963, filed Dec. 2, 1999, entitled: *Expendable/Retractable Stent For Venous And Valvular Annulus Use*.

* cited by examiner

MEDICAL DEVICE AND METHODS OF USE OF GLAUCOMA TREATMENT

RELATED APPLICATIONS

This application claims the benefit of U.S. Provisional Application No. 60/288,325, filed May 3, 2001, entitled MEDICAL DEVICE AND METHODS OF USE FOR GLAUCOMA TREATMENT, the entire contents of which are hereby incorporated by reference herein.

BACKGROUND OF THE INVENTION

1. Field of the Invention

The invention relates generally medical devices and methods for the treatment of glaucoma in an animal eye and, more particularly, to medical devices and methods for treating tissue of the trabecular meshwork and/or Schlemm's canal of the eye to restore or rejuvenate a portion or all of the normal physiological function of directing aqueous outflow for maintaining a normal intraocular pressure in the eye.

2. Description of the Related Art

The human eye is a specialized sensory organ capable of light reception and able to receive visual images. The trabecular meshwork serves as a drainage channel and is located in anterior chamber angle formed between the iris and the cornea. The trabecular meshwork maintains a balanced pressure in the anterior chamber of the eye by draining aqueous humor from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is a constant flow of aqueous humor from the ciliary body to the eye's front chamber. The eye's pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

Current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs.

When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10–15%); infection (a life long risk of 2–5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Trabeculopuncture: Q-switched Neodynium (Nd) YAG lasers also have been investigated as an optically invasive technique for creating full-thickness holes in trabecular meshwork. However, the relatively small hole created by this trabeculopuncture technique exhibits a filling-in effect and fails.

Goniophotoablation/Laser Trabecular Ablation: Goniophotoablation is disclosed by Berlin in U.S. Pat. No. 4,846, 172 and involves the use of an excimer laser to treat glaucoma by ablating the trabecular meshwork. This was demonstrated not to succeed by clinical trial. Hill et al. used an Erbium:YAG laser to create full-thickness holes through trabecular meshwork (Hill et al., Lasers in Surgery and Medicine 11:341–346, 1991). This technique was investigated in a primate model and a limited human clinical trial at the University of California, Irvine. Although morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage: This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanulostomy (VC) and non-penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous humor is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous humor through the surgical opening will continue. The risk of placing a glaucoma drainage device also includes hemorrhage, infection, and diplopia (double vision).

Examples of implantable shunts and surgical methods for maintaining an opening for the release of aqueous humor from the anterior chamber of the eye to the sclera or space beneath the conjunctiva have been disclosed in, for example, U.S. Pat. No. 6,059,772 to Hsia et al., and U.S. Pat. No. 6,050,970 to Baerveldt.

All of the above surgeries and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have prompted ophthalmic surgeons to find other approaches to lowering intraocular pressure or treating tissue of trabecular meshwork.

The trabecular meshwork and juxtacanilicular tissue together provide the majority of resistance to the outflow of aqueous and, as such, are logical targets for tissue stimulation and/or rejuvenating in the treatment of open-angle glaucoma. In addition, minimal amounts of tissue are displaced and functions of the existing physiologic outflow pathways are restored.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to search for new surgical approaches that may provide better and safer care for patients with glaucoma.

Therefore, there is a great clinical need for a method of treating glaucoma that is faster, safer, and less expensive than currently available drug or surgical modalities.

SUMMARY OF THE INVENTION

The trabecular meshwork and juxtacanilicular tissue together provide the majority of resistance to the outflow of aqueous and, as such, are logical targets for tissue stimulation and/or rejuvenating in the treatment of glaucoma. Various embodiments of glaucoma devices and methods are disclosed herein for rejuvenating the physiological functions of the trabecular meshwork by therapeutically reversing the aqueous flow through the trabecular meshwork, or applying vibrational energy to tissue of trabecular meshwork effective to reduce intraocular pressure (IOP).

Copending U.S. application Ser. No. 09/704,276, filed Nov. 1, 2000, entitled GLAUCOMA TREATMENT DEVICE, disclose devices and methods of placing a trabecular shunt ab interno, i.e., from inside the anterior chamber through the trabecular meshwork, into Schlemm's canal. The entire contents of this copending patent application are hereby incorporated by reference herein. The invention encompasses both ab interno and ab externo glaucoma shunts and methods thereof.

One technique performed in accordance with aspects herein may be referred to generally as "trabecular bypass surgery." Advantages of this type of surgery include lowering intraocular pressure in a manner which is simple, effective, disease site-specific, and can potentially be performed on an outpatient basis.

Generally, trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated device is placed within the hole and serves as a stent. U.S. patent application Ser. No. 09/549,350, filed Apr. 14, 2000, entitled APPARATUS AND METHOD FOR TREATING GLAUCOMA, the entire contents of which are hereby incorporated by reference herein, discloses trabecular bypass surgery.

Some aspects of the invention relate to a medical device system for treating tissue of trabecular meshwork of an eye comprising aspiration means for inducing a liquid flow through the trabecular meshwork in an opposite direction of a physiological aqueous outflow pathway. In one embodiment, the aspiration means comprises an elongated tubular member having a proximal end, a distal end and an inflatable cup balloon mounted at the distal end, wherein the cup balloon has a balloon rim defining an isolated enclosure adapted for inducing the liquid flow through the trabecular meshwork by a suction power exerted at the proximal end.

Some aspects of the invention relate to a method for treating tissue of trabecular meshwork of an eye comprising directing a liquid flow through the trabecular meshwork in an opposite direction of a physiological aqueous outflow pathway. In one embodiment, the aspiration means are provided for directing a liquid flow through the trabecular meshwork in an opposite direction of the physiological aqueous outflow pathway.

Some aspects of the invention relate to a medical device for treating tissue of trabecular meshwork of an eye comprising an ultrasound arrangement on the medical device for providing ultrasonic vibrational energy to stimulate the tissue of the trabecular meshwork. In one embodiment, the device is positioned inside Schlemm's canal in an ab externo procedure. In another embodiment, the device is positioned through the trabecular meshwork in an ab interno procedure.

Some aspects of the invention relate to a medical device for treating tissue of trabecular meshwork of an eye comprising a fiber optic arrangement on the medical device for providing light imaging function for tissue characterization. In one embodiment, the light imaging function comprises a near infrared Raman spectroscopy.

In accordance with some embodiments, medical devices and methods are provided for treating tissue of the trabecular meshwork and/or Schlemm's canal of an eye to restore or rejuvenate a portion or all of the normal physiological function of directing aqueous outflow for maintaining a normal intraocular pressure in the eye.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

The preferred embodiments of the invention described herein relate particularly to surgical and therapeutic treatment of glaucoma through reduction of intraocular pressure and stimulation and/or rejuvenation of the trabecular meshwork tissue. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
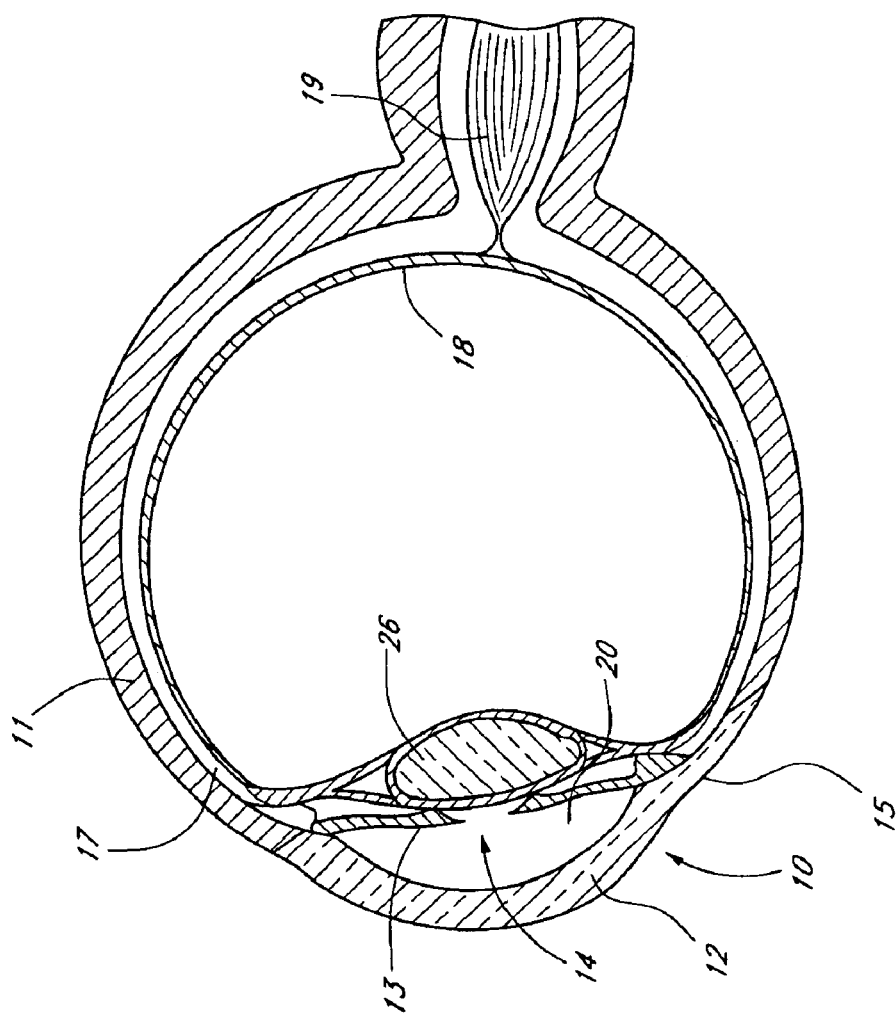
FIG. 1 is a coronal or sagittal cross-sectional view of an eye.
Figure 2:
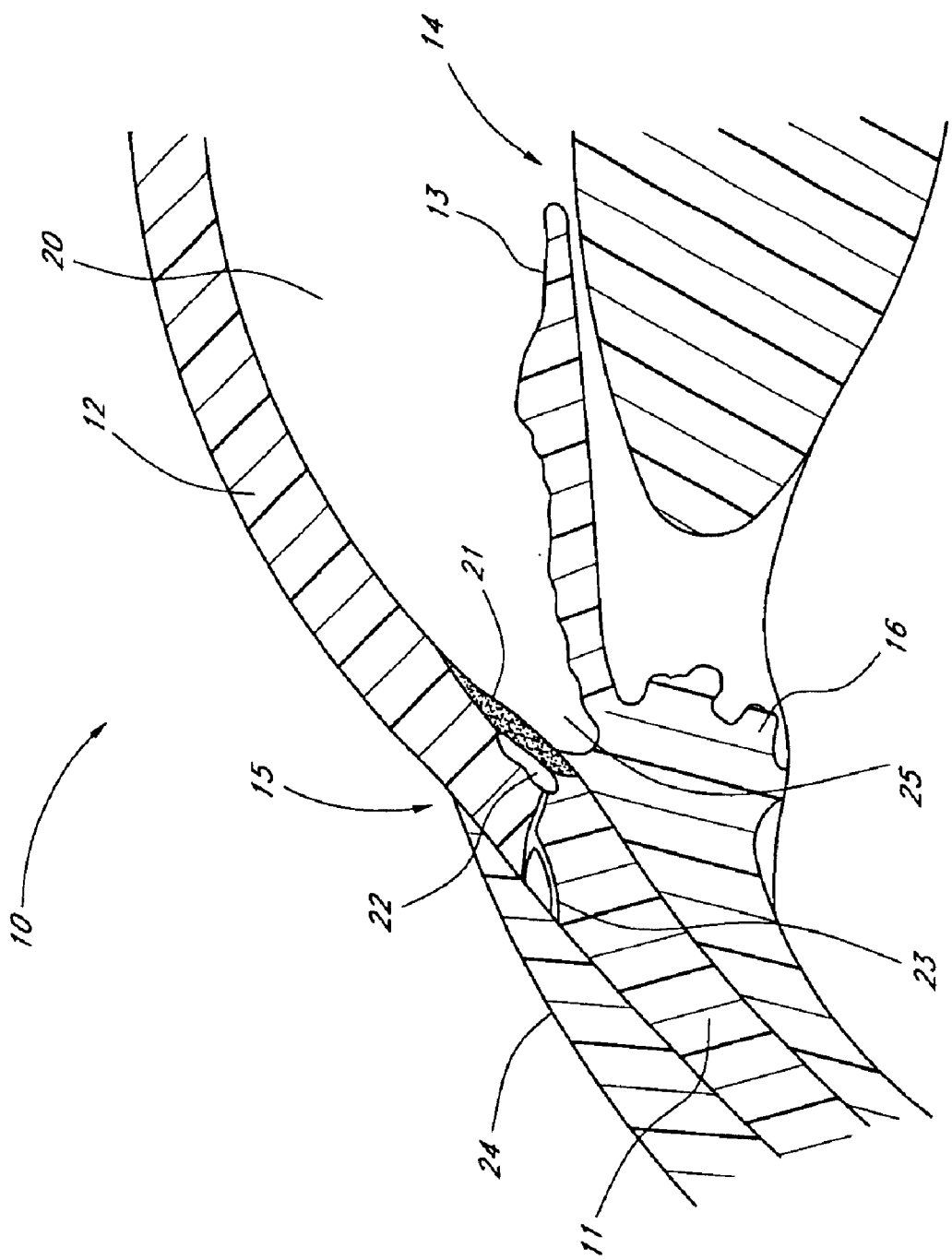
FIG. 2 is an enlarged cross-sectional view of an anterior chamber angle of the eye of FIG. 1.

FIG. 1 is a cross-sectional view of an eye 10, while FIG. 2 is a close-up view showing the relative anatomical locations of a trabecular meshwork 21, an anterior chamber 20, and Schlemm's canal 22. A sclera 11 is a thick collagenous tissue which covers the entire eye 10 except a portion which is covered by a cornea 12.

Referring to FIGS. 1 and 2, the cornea 12 is a thin transparent tissue that focuses and transmits light into the eye and through a pupil 14, which is a circular hole in the center of an iris 13 (colored portion of the eye). The cornea 12 merges into the sclera 11 at a juncture referred to as a limbus 15. A ciliary body 16 extends along the interior of the sclera 11 and is coextensive with a choroid 17. The choroid 17 is a vascular layer of the eye 10, located between the sclera 11 and a retina 18. An optic nerve 19 transmits visual information to the brain and is the anatomic structure that is progressively destroyed by glaucoma.

Still referring to FIGS. 1 and 2, the anterior chamber 20 of the eye 10, which is bound anteriorly by the cornea 12 and posteriorly by the iris 13 and a lens 26, is filled with aqueous humor (also referred to as "aqueous" herein). Aqueous is produced primarily by the ciliary body 16, then moves anteriorly through the pupil 14 and reaches an anterior chamber angle 25, formed between the iris 13 and the cornea 12.

As best illustrated by the drawing of FIG. 2, in a normal eye, aqueous is removed from the anterior chamber 20 through the trabecular meshwork 21. Aqueous passes through the trabecular meshwork 21 into Schlemm's canal 22 and thereafter through a plurality of aqueous veins 23, which merge with blood-carrying veins, and into systemic venous circulation. Intraocular pressure is maintained by an intricate balance between secretion and outflow of aqueous in the manner described above. Glaucoma is, in most cases, characterized by an excessive buildup of aqueous in the anterior chamber 20 which leads to an increase in intraocular pressure. Fluids are relatively incompressible, and thus intraocular pressure is distributed relatively uniformly throughout the eye 10.

As shown in FIG. 2, the trabecular meshwork 21 is adjacent a small portion of the sclera 11. Exterior to the sclera 11 is a conjunctiva 24. Traditional procedures that create a hole or opening for implanting a device through the tissues of the conjunctiva 24 and sclera 11 involve extensive surgery, as compared to surgery for implanting a device, as described herein, which ultimately resides entirely within the confines of the sclera 11 and cornea 12.

Figure 3:
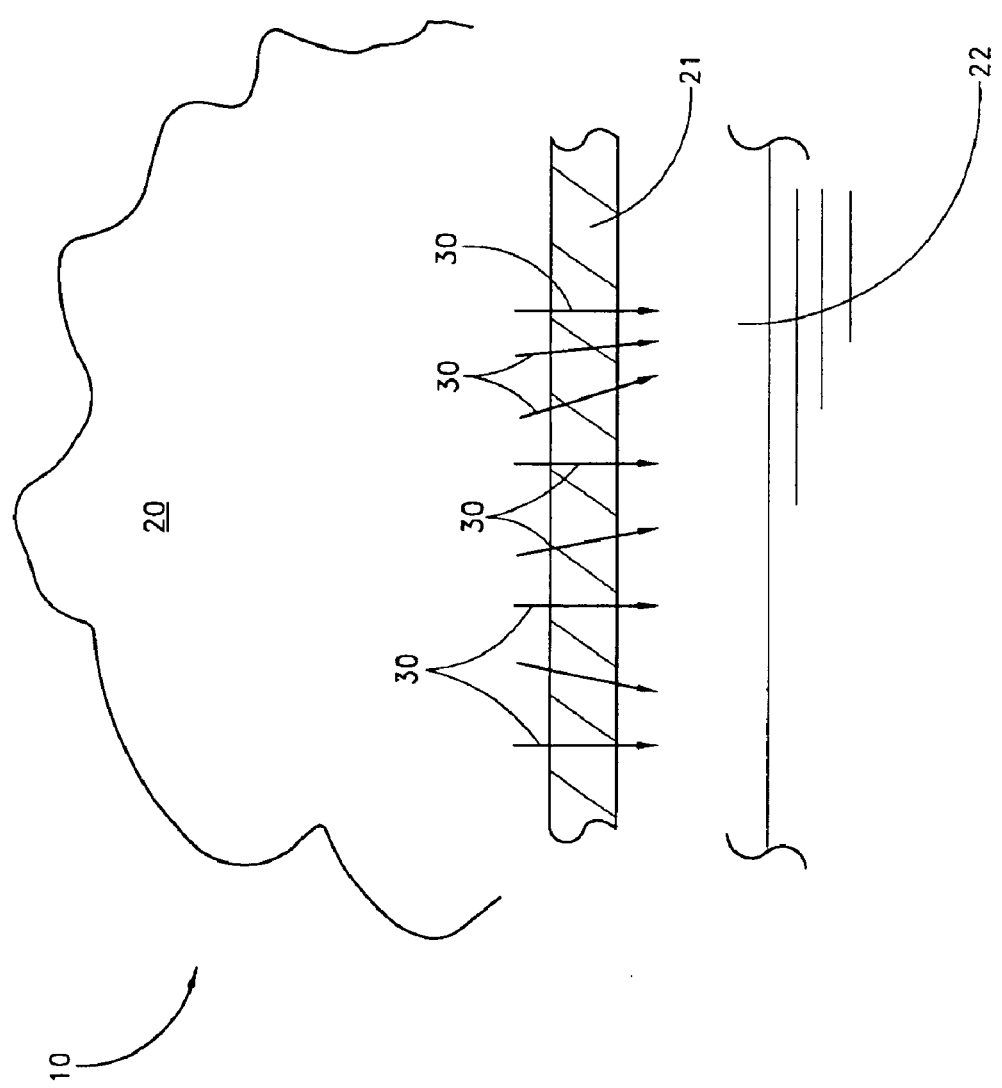
FIG. 3 is a simplified partial view of an eye schematically illustrating the outflow pathway of aqueous through trabecular meshwork under normal physiological conditions.

FIG. 3 is a simplified partial view of an eye 10 schematically illustrating the outflow pathway of aqueous under normal physiological conditions. The direction of flow is generally indicated by arrows 30. As discussed above, in a normal eye, aqueous is removed from the anterior chamber 20 through the trabecular meshwork 21. Aqueous then passes through the trabecular meshwork 21 into Schlemm's canal 22 and thereafter eventually into systemic venous circulation. The flow of aqueous or other liquids through the trabecular meshwork 21 is sometimes referred to as "trabecular outflow" herein.

Reversed Trabecular Outflow

The embodiments of FIGS. 4–7 illustrate aspects and features of flushing or treating the trabecular meshwork by providing a flow through all or part of the trabecular meshwork in the opposite direction to that normally experienced by the trabecular meshwork during normal physiological function. That is, in a direction generally opposite to or against a normal outflow such as the outflow pathway under normal physiological conditions illustrated in FIG. 3.

Some purposes for this treatment are (i) to administer medication or other therapeutic agents to the meshwork or lining of Schlemm's canal; (ii) to flush out debris that may be occluding the meshwork or Schlemm's canal; (iii) to open channels through the meshwork and endothelial layer to improve outflow; or (iv) to stimulate or rejuvenate the tissue of trabecular meshwork for restoring its normal physiological function. Advantageously, and as discussed further below, trabecular meshwork flushing flow allows an ab interno or ab externo procedure for stimulating and/or treating the dysfunctional trabecular meshwork.

Certain embodiments of such medication or other therapeutic agents for treating trabecular meshwork or lining of Schlemm's canal are disclosed in copending U.S. application Ser. No. 10/046,137, filed Nov. 8, 2001, entitled DRUG-RELEASE TRABECULAR IMPLANT FOR GLAUCOMA TREATMENT, the entire contents of which are hereby incorporated by reference herein. As discussed in further detail later herein, in accordance with some embodiments, a therapeutic liquid is introduced through an inlet port of a medical device system (described below) for providing a liquid back flow or reversed outflow through the trabecular meshwork in an opposite direction to that of the physiological aqueous outflow pathway.

The therapeutic liquid may comprise a pharmaceutical substance selected from a group consisting of Imidazole antiproliferative agents, quinoxoalines, phsophonyl-methoxyalkyl nucleotide analogs and related nucleotide analogs, potassium channel blockers, synthetic oligonucleotides, Transforming Growth Factor-beta (TGF-beta), 5-[1-hydroxy-2-[2-(2-methoxyphenoxyl)ethylamino]ethyl]-2-methylbenzenesulfonamide, guanylate cyclase inhibitors, methylene blue, butylated hydroxyanisole, and N-methylhydroxylamine, 2-(4-methylaminobutoxy)diphenylmethane, a combination of apraclonidine and timolol, cloprostenol analogs or fluprostenol analogs, an ophthalmic composition that provides a sustained release of a water soluble medicament, said water soluble medicament comprising a crosslinked carboxy-containing polymer, a sugar, and water, a non-corneotoxic serine-threonine kinase inhibitor, a composition of non-steroidal glucocorticoid antagonist, and a prostaglandin analog or a derivative thereof.

Ab Interno Global Trabecular Meshwork Flush/Treatment

Figure 4:
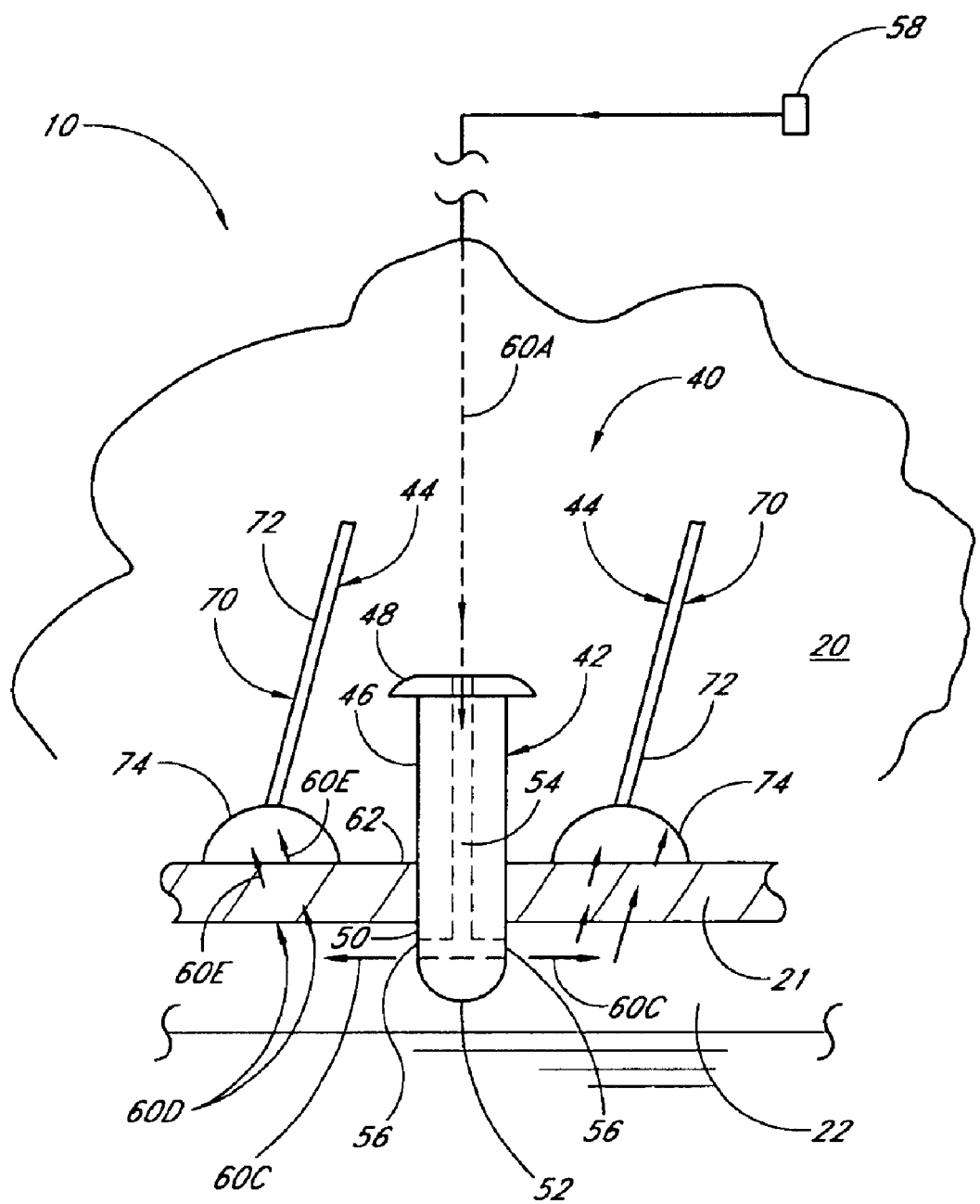
FIG. 4 is a simplified partial view of an eye schematically illustrating the placement and use of a system therein for reversing trabecular outflow to rejuvenate dysfunctional trabecular meshwork utilizing an ab interno procedure and having features and advantages in accordance with one embodiment of the invention.

FIG. 4 is a simplified partial view of an eye 10 generally illustrating the placement and use of a medical device system 40 therein for reversing trabecular outflow and having features and advantages in accordance with one embodiment. The system 40 generally comprises a trabecular device 42 for establishing an outflow pathway and a reversed trabecular flushing flow (that is, in a direction generally opposite to or against a normal outflow such as the outflow pathway under normal physiological conditions illustrated in FIG. 3). In one embodiment, the system 40 further comprises aspiration means 44 for treating tissue of the trabecular meshwork 21 of the eye 10 by inducing a liquid flow through the trabecular meshwork 21 in an opposite direction to that of a physiological aqueous outflow pathway.

Referring to FIG. 4, the system 40 reverses the outflow to stimulate or rejuvenate the dysfunctional trabecular meshwork. The term "rejuvenate" is herein generally intended to mean to restore a part or all of the normal physiological function. Stated differently, the use of the term "rejuvenate" denotes at least some or full restoration of the normal physiological function.

In the illustrated embodiment of FIG. 4, the trabecular device 42 generally comprises an elongate body having a proximal section 46 with a proximal end 48, a distal section 50 and a distal end 52, and a lumen 54 extending therethrough and terminating in one or more outlet ports 56. Aqueous or other liquid flows into the lumen 54 at the proximal end 48 and exits through the one or more outlet ports 56.

As shown in the embodiment of FIG. 4, the trabecular device 42 is inserted through the trabecular meshwork 21 so that the distal section 50 is positioned inside Schlemm's canal 22 utilizing an ab interno procedure. To facilitate the trabecular flow through the trabecular device 42, a liquid inlet port 58 of the device 40 is generally placed outside the eye 10 for introducing a pressurized therapeutic liquid flow while the one or more liquid outlet ports 56 of the trabecular device 42 are generally positioned within Schlemm's canal 22.

Referring to FIG. 4, the flushing flow originates from the anterior chamber 20 or from an external irrigation applicator (as generally indicated by arrow 60A), enters the trabecular device 42 (as generally indicated by arrow 60B), enters Schlemm's canal 22 through the one or more outlet ports 56 (as generally indicated by arrows 60C), reversibly passes through the trabecular meshwork 21 (as generally indicated by arrows 60D) into the anterior chamber 20 or into the aspiration means 44 within the anterior chamber 20 (as generally indicated by arrows 60E). The reverse flushing outflow or backflow is created by a pressure difference, differential or gradient created between a higher pressure in Schlemm's canal and a lower pressure in the anterior chamber 20 or in the aspiration means 44.

As indicated above, in accordance with one embodiment, to facilitate and enhance the flushing back flow (or reversed outflow) to travel effectively through the trabecular meshwork 21, aspiration means 44 are provided at the surface 62 of the trabecular meshwork 21 exposed to the anterior chamber 20. The aspiration means 44 induce a liquid flow through the trabecular meshwork in an opposite direction to that of a physiological aqueous outflow pathway.

Figure 5:
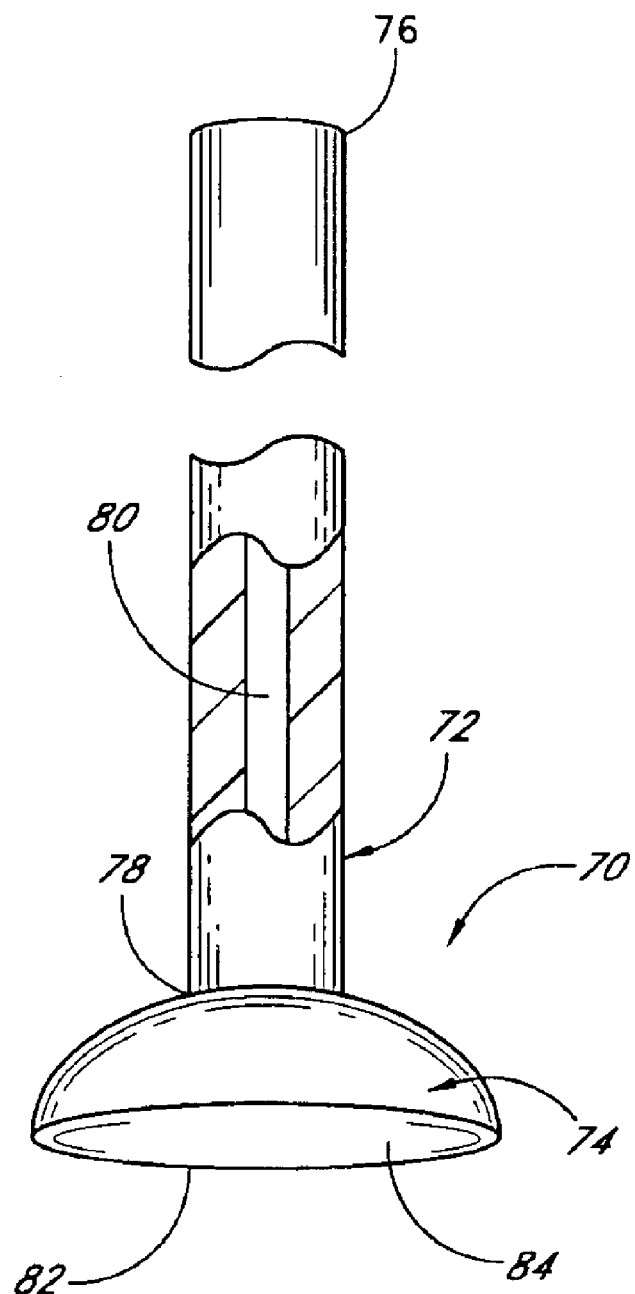
FIG. 5 is a simplified enlarged view of an aspiration means of the system of FIG. 4 for enhancing the flow reversal through the trabecular meshwork.

Referring to FIGS. 4 and 5, in accordance with one embodiment, the aspiration means 44 comprises one or more suction devices 70 which are placed on the top surface 62 of the trabecular meshwork 21. The suction device 70 generally comprises an elongated tubular member, introducer or irrigating applicator 72 and an inflatable cup or cone balloon 74.

Still referring to FIGS. 4 and 5, the tubular member 72 has a proximal end 76, a distal end 78 and a lumen 80 extending therethrough. The inflatable cup balloon 74 is mounted at the distal end 78. The cup balloon 74 has a balloon rim 82 defining an isolated enclosure 84 for aspiration of fluid through the lumen 80 of the introducer 72. The enclosure 84 is adapted for inducing liquid flow through the trabecular meshwork 21 and into the lumen 80 by suction power (e.g., by creating a partial vacuum or reduced pressure relative to the appropriate ambient pressure) exerted at the proximal end 76. The device 70 is preferably used in an ab interno procedure.

The inflatable balloon 72 (FIGS. 4 and 5) and its principles for forming an isolated enclosure 84 by an inflating fluid are well known to one of ordinary skill in the art. During the entry and exit phases of the device 70 into and out of the eye 10, the balloon 72 is preferably in a collapsed or compact state to have a low profile adapted for easy insertion and withdrawal.

The embodiment as shown in FIG. 4 enables a completely ab interno procedure that advantageously acts on or treats the majority and substantially all of the trabecular meshwork 21. As discussed above, it is one embodiment of flushing or treating the trabecular meshwork 21 by providing a flow through all or part of the trabecular meshwork 21 in the opposite direction to that normally experienced by trabecular meshwork 21 during normal physiological function. The trabecular device 42 and the aspiration means 44 of the system 40 are both inserted in an ab interno procedure.

This procedure of the embodiments of FIGS. 4 and 5 may optionally be combined with an episcleral ring that is pressed onto the eye to occlude the venous system downstream of the collector channels. Advantageously, this further assists in achieving the pressures that are sufficiently high to provide effective back flow through the trabecular meshwork 21 by creating a desirable pressure difference, differential or gradient which drives the reversed outflow.

It is one object to provide a method for treating tissue of trabecular meshwork of an eye comprising directing a liquid flow through the trabecular meshwork in an opposite direction to that of a physiological aqueous outflow pathway. The method further comprises aspiration means for directing a liquid flow through the trabecular meshwork in an opposite direction of the physiological aqueous outflow pathway, wherein the aspiration means may comprise an elongated tubular member having a proximal end, a distal end and an inflatable cup balloon mounted at the distal end, wherein the cup balloon has a balloon rim defining an isolated enclosure adapted for inducing the liquid flow through the trabecular meshwork by a suction power exerted at the proximal end.

Ab Externo Trabecular Meshwork Flush/Treatment

Lynch and Brown in PCT Publication No. WO 00/64389, published Nov. 2, 2000, entitled TRABECULOTOMY DEVICE AND METHOD FOR TREATING GLAUCOMA, PCT Publication No. WO 00/64390, published Nov. 2, 2000, entitled INFLATABLE DEVICE AND METHOD FOR TREATING GLAUCOMA, PCT Publication No. WO 00/64391, published Nov. 2, 2000, entitled STENT DEVICE AND METHOD FOR TREATING GLAUCOMA, and PCT Publication No. WO 00/64393, published Nov. 2, 2000, entitled SHUNT DEVICE AND METHOD FOR TREATING GLAUCOMA, the entire contents of each one of which are hereby incorporated by reference herein, disclose devices and methods for entering Schlemm's canal in an ab externo manner for treating glaucoma.

Figure 6:
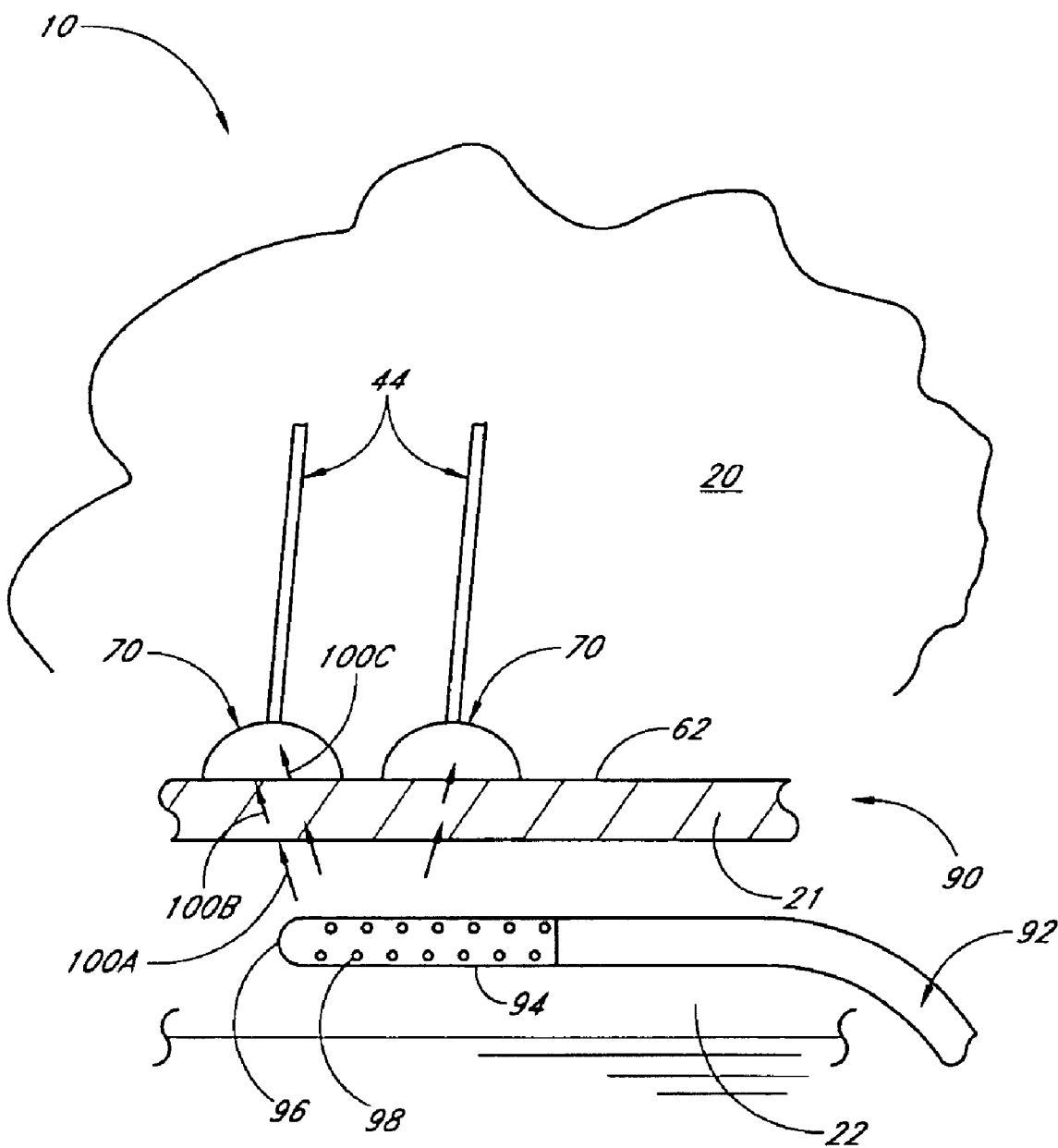
FIG. 6 is a simplified partial view of an eye schematically illustrating the placement and use of a system therein for reversing trabecular outflow to stimulate and/or rejuvenate dysfunctional trabecular meshwork utilizing an ab externo catheter method and having features and advantages in accordance with one embodiment of the invention.

FIG. 6 is a simplified partial view of an eye 10 generally illustrating the placement and use of a medical device system 90 therein for reversing trabecular outflow and having features and advantages in accordance with one embodiment. The system 90 generally comprises a catheter-type device 92 for establishing a reversed trabecular flushing flow (that is, in a direction generally opposite to or against a normal outflow such as the outflow pathway under normal physiological conditions illustrated in FIG. 3). In one embodiment, the system 90 further comprises aspiration means 44 for treating tissue of the trabecular meshwork 21 of the eye 10 by inducing a liquid flow through the trabecular meshwork 21 in an opposite direction to that of a physiological aqueous outflow pathway.

Referring to FIG. 6, the inflow catheter 92 can be inserted into Schlemm's canal 22 either via an external incision that unroofs the Schlemm's canal 22 or through an episcleral vein (or other blood vessel downstream in the circulatory system) to a collector channel then into Schlemm's canal 22. The outflow portion of the instrument, that is, the aspiration means 44, is placed in the anterior chamber 20 to take up the fluid volume that passes through the trabecular meshwork 21.

In the illustrated embodiment of FIG. 6, the catheter device 92 generally comprises a distal section 94, a distal end 96 and a plurality of micropores 98 on the distal section for liquid flow. Preferably, the aspiration means 44 comprises one or more inflatable balloon type suction devices 70 (discussed above in reference to FIG. 5) which are placed on the top surface 62 of the trabecular meshwork 21.

Referring to the embodiment of FIG. 6, the catheter device 92 is inserted from a puncture at the scleral wall of the eye 10 by an ab externo procedure so that the distal section 94 is positioned in Schlemm's canal 22. By maintaining a pressure difference between Schlemm's canal 22 and the anterior chamber 20, a reversed trabecular flow or back flow (as generally indicated by arrows 100A, 100B, and 100C) is created from Schlemm's canal 22 through the trabecular meshwork 21 and into the anterior chamber 20 or the aspiration means 44. The reverse flushing outflow or backflow is created by a pressure difference, differential or gradient created between a higher pressure in Schlemm's canal 22 and a lower pressure in the anterior chamber 20 or in the aspiration means 44.

As indicated above, in accordance with one embodiment, to facilitate and enhance the flushing back flow (or reversed outflow) to travel effectively through the trabecular meshwork 21, aspiration means 44 (FIG. 6) are provided at the surface 62 of the trabecular meshwork 21 exposed to the anterior chamber 20. The aspiration means 44 induce a liquid flow through the trabecular meshwork 21 in an opposite direction to that of a physiological aqueous outflow pathway.

The embodiment shown in FIG. 6 enables a combined ab externo catheter procedure with an ab interno aspiration means that act on or treat all or part of the trabecular meshwork 21. Since the pressure in Schlemm's canal 22 is kept at a relatively high value, it is also used to stimulate the dysfunctional tissue inside Schlemm's canal 22, the collector channels or the trabecular meshwork 21. This method is well suited to cases wherein the Schlemm's canal 22 has shrunk as in trabeculectomy patients.

This procedure of the embodiment of FIG. 6 may optionally be combined with an episcleral ring that is pressed onto the eye to occlude the venous system downstream of the collector channels. Advantageously, this further assists in achieving the pressures that are sufficiently high to provide effective back flow through the trabecular meshwork 21 by creating a desirable pressure difference, differential or gradient which drives the reversed outflow.

Figure 7:
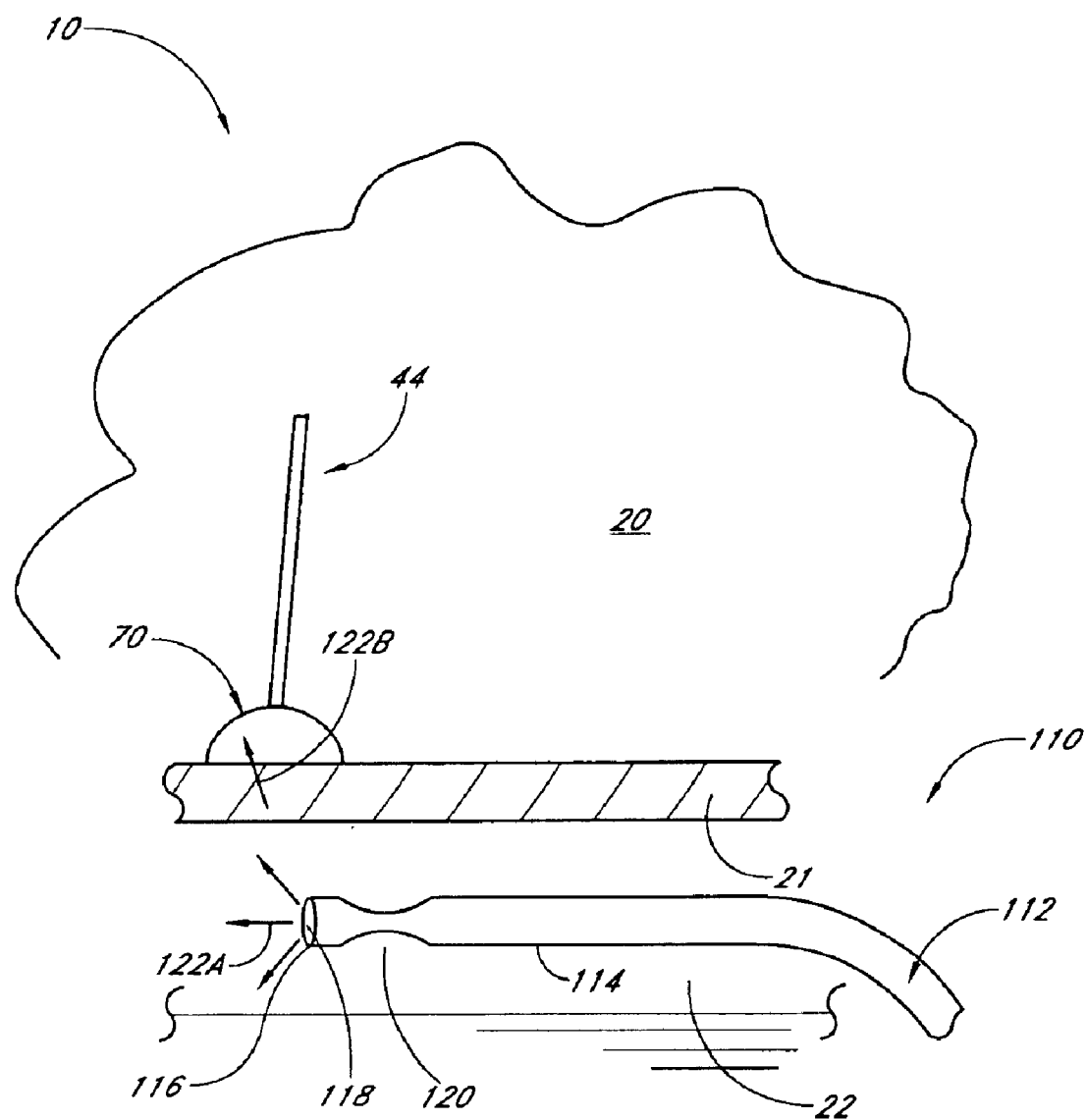
FIG. 7 is a simplified partial view of an eye schematically illustrating the placement and use of a system therein for reversing trabecular outflow to stimulate and/or rejuvenate dysfunctional trabecular meshwork utilizing an ab externo jet stream method and having features and advantages in accordance with one embodiment of the invention.

FIG. 7 is a simplified partial view of an eye 10 generally illustrating the placement and use of a medical device system 110 therein for reversing trabecular outflow and having features and advantages in accordance with one embodiment. The system 110 generally comprises a catheter-type device 112 for establishing a reversed trabecular flushing flow (that is, in a direction generally opposite to or against a normal outflow such as the outflow pathway under normal physiological conditions illustrated in FIG. 3). In one embodiment, the system 110 further comprises aspiration means 44 for treating tissue of the trabecular meshwork 21 of the eye 10 by inducing a liquid flow through the trabecular meshwork 21 in an opposite direction to that of a physiological aqueous outflow pathway.

Referring to FIG. 7, the inflow catheter 112 can be inserted into Schlemm's canal 22 either via an external incision that unroofs the Schlemm's canal 22 or through an episcleral vein (or other blood vessel downstream in the circulatory system) to a collector channel then into Schlemm's canal 22. The outflow portion of the instrument, that is, the aspiration means 44, is placed in the anterior chamber 20 to take up the fluid volume that passes through the trabecular meshwork 21.

In the illustrated embodiment of FIG. 7, the catheter device 112 generally comprises a distal section 114, a distal end 116 with a distal opening 118 and a throttle or narrowed neck 120 at about or slightly downstream of the distal opening 118 for creating a liquid jet effective for therapeutic purposes. The configuration of the throttle or nozzle 120 can be used to control the characteristics of the liquid jet emanating from the distal opening 118. Preferably, the aspiration means 44 comprises one or more inflatable balloon type suction devices 70 (discussed above in reference to FIG. 5) which are placed on the top surface 62 of the trabecular meshwork 21.

Referring to the embodiment of FIG. 7, the catheter device 112 is inserted from a puncture at the scleral wall of the eye 10 by an ab externo procedure so that the waterjet catheter tip 114 is positioned in Schlemm's canal 22. By maintaining a pressure difference between Schlemm's canal 22 and the anterior chamber 20, a reversed trabecular flow or back flow (as generally indicated by arrows 122A, 122B) is created from Schlemm's canal 22 through the trabecular meshwork 21 and into the anterior chamber 20 or the aspiration means 44. The reverse flushing outflow or backflow is created by a pressure difference, differential or gradient created between a higher pressure in Schlemm's canal 22 and a lower pressure in the anterior chamber 20 or in the aspiration means 44.

The embodiment of FIG. 7 may also comprise injecting a therapeutic agent, such as steroids, growth factors, angiogenic inhibitors and the like through the catheter device 112 for enhancing tissue rejuvenation or stimulation. These agents, water or other liquids may be provided in the form of a cooled and/or heated flow, as needed or desired, to further enhance tissue rejuvenation or stimulation. The jetted flow may also be used to scour the inner wall of Schlemm's canal 22 and adjacent trabecular meshwork 21.

As indicated above, in accordance with one embodiment, to facilitate and enhance the flushing back flow (or reversed outflow) to travel effectively through the trabecular meshwork 21, aspiration means 44 (FIG. 7) are provided at the surface 62 of the trabecular meshwork 21 exposed to the anterior chamber 20. The aspiration means 44 induce a liquid flow through the trabecular meshwork 21 in an opposite direction to that of a physiological aqueous outflow pathway.

The embodiment shown in FIG. 7 enables a combined ab externo catheter procedure with an ab interno aspiration means that act on or treat all or part of the trabecular meshwork 21. Since the pressure in Schlemm's canal 22 is kept at a relatively high value, it is also used to stimulate the dysfunctional tissue inside Schlemm's canal 22, the collector channels or the trabecular meshwork 21. This method is well suited to cases wherein the Schlemm's canal 22 has shrunk as in trabeculectomy patients.

This procedure of the embodiment of FIG. 7 may optionally be combined with an episcleral ring that is pressed onto the eye to occlude the venous system downstream of the collector channels. Advantageously, this further assists in achieving the pressures that are sufficiently high to provide effective back flow through the trabecular meshwork 21 by creating a desirable pressure difference, differential or gradient which drives the reversed outflow.

Schlemm's Canal and/or Trabecular Meshwork Treatment

Figure 8:
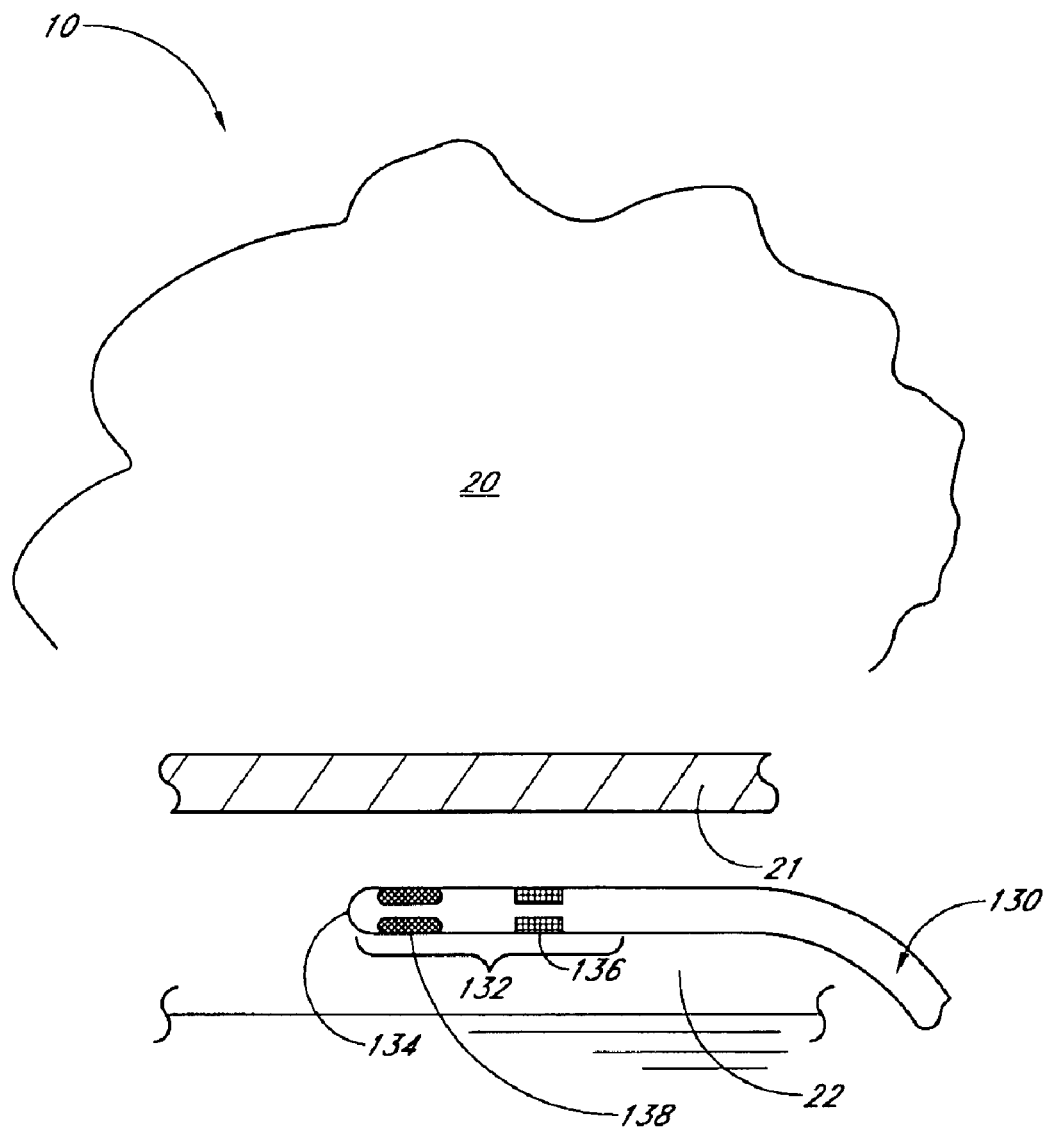
FIG. 8 is a simplified partial view of an eye schematically illustrating the placement and use of a system therein for rejuvenating dysfunctional trabecular meshwork by an ab externo vibrational energy method and having features and advantages in accordance with one embodiment of the invention.

FIG. 8 is a simplified partial view of an eye 10 generally illustrating the placement and use of a system or device 130 therein for rejuvenating dysfunctional trabecular meshwork by an ab externo vibrational energy method and having features and advantages in accordance with one embodiment. The ultrasound catheter device 130 is inserted into Schlemm's canal 22 by an ab externo procedure.

In the illustrated embodiment of FIG. 8, the ultrasound catheter device 130 generally comprises a catheter tip or distal section 132, a distal end 134 and one or more ultrasound transducers 136 on the distal section 132. As shown in FIG. 8, the ultrasound catheter tip section 132 is inserted into Schlemm's canal 22.

Referring to FIG. 8, the ultrasound transducer 136 is used to heat or cause vibrations to the inner wall of Schlemm's canal 22 and the adjacent trabecular meshwork 21. The effected stimulation of these tissues provides generally improved flow into Schlemm's canal by reducing the resistance to outflow and/or due to more effective fluid transmission after tissue rejuvenation. An additional set of imaging transducers 138 may be mounted at about the tip section 132 of the catheter device 130 proximate to the distal end 134 for catheter deployment and positioning purposes.

Figure 9:
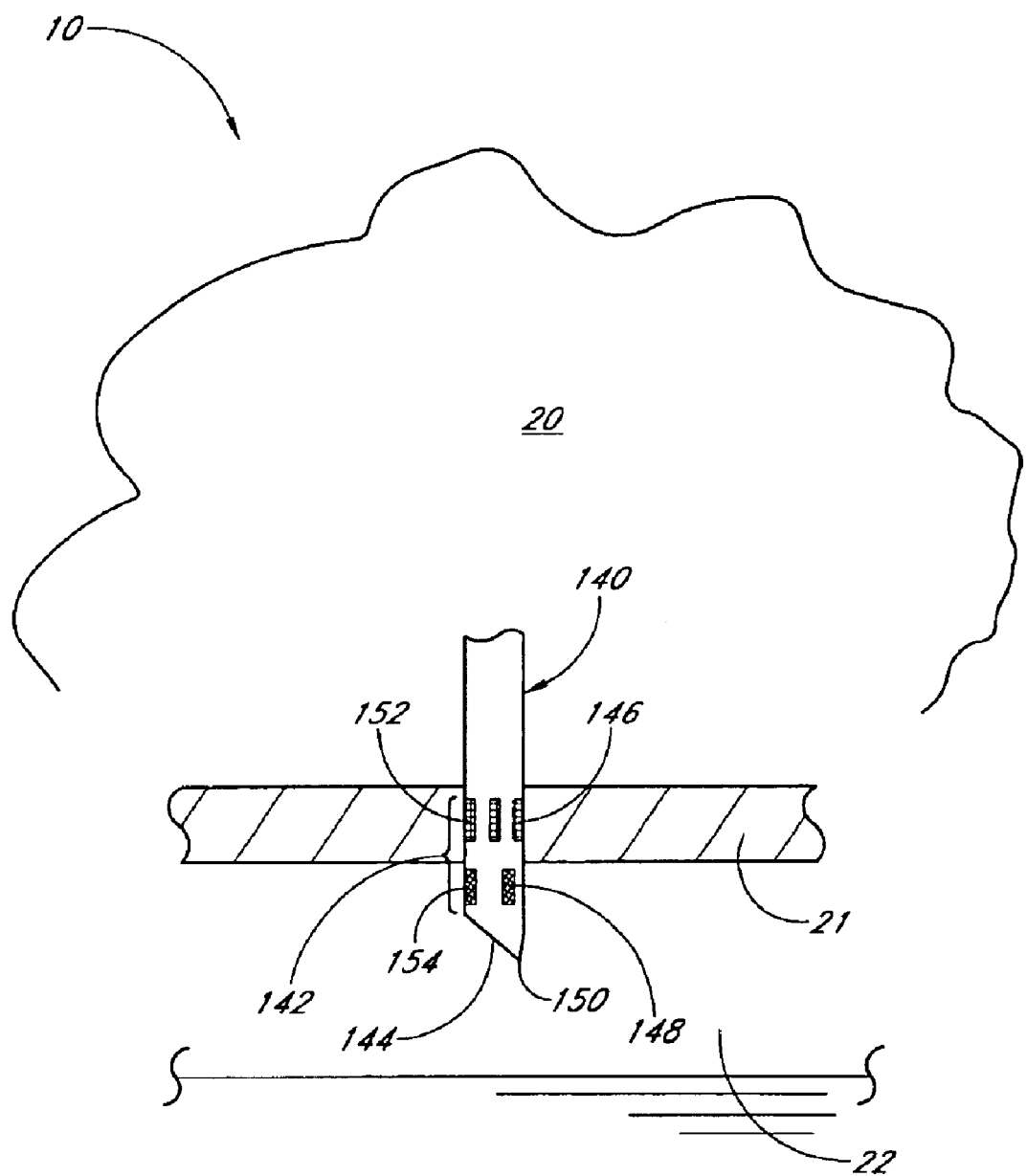
FIG. 9 is a simplified partial view of an eye schematically illustrating the placement and use of a system therein for rejuvenating dysfunctional trabecular meshwork by an ab interno vibrational energy method and having features and advantages in accordance with one embodiment of the invention.

FIG. 9 is a simplified partial view of an eye 10 generally illustrating the placement and use of a system or ultrasound device 140 therein for rejuvenating dysfunctional trabecular meshwork by an ab interno vibrational energy method and having features and advantages in accordance with one embodiment. The ultrasound device 140 generally comprises a tip or distal section 142, a distal end 144, a therapeutic ultrasound arrangement 146 and an imaging ultrasound arrangement 148.

In the illustrated embodiment, the device 140 (FIG. 9) is inserted from an incision at the cornea wall of the eye 10 and advanced through the anterior chamber 20 to the trabecular meshwork 21. An optional self-trephine cutting tip 150 creates an opening through the trabecular meshwork 21.

Referring to FIG. 9, the therapeutic ultrasound arrangement 146 generally comprises one or more ultrasound transducers 152. The ultrasound arrangement 146 is positioned at an appropriate location about the trabecular meshwork 21 and is used to heat or cause vibrations to the tissue of the adjacent trabecular meshwork 21 for tissue stimulation and/or rejuvenating.

Still referring to FIG. 9, the imaging ultrasound arrangement 148 generally comprises one or more imaging transducers 154. The imaging arrangement is located at about the tip section 142 of the device 140 proximate to the distal end 144 for guiding the deployment and positioning.

Of course, as the skilled artisan will appreciate, that the ultrasound arrangement 146 (FIG. 9) may rest at any suitable position within trabecular meshwork 21, as needed or desired. Also, the therapeutic ultrasound arrangement 146 may extend into Schlemm's canal 22, as needed or desired. The length, size, and space of the ultrasound transducers 152 of the arrangement 146 may be efficaciously adjusted to achieve the desired stimulating and/or rejuvenating effects.

Newman et al. in U.S. Pat. No. 6,372,498, the entire contents of which are hereby incorporated by reference herein, discloses an ultrasound system that applies vibrational energy at a specific range of frequency and intensity to enhance nucleic acid transfection of vascular smooth muscle cells.

Tissues possess three important properties that are of fundamental importance in ultrasound imaging. These are attenuation, reflectivity, and speed of sound. Some ultrasound energy that is absorbed by tissue is converted to heat adapted for therapeutically treating a dysfunctional trabecular meshwork. In another aspect, ultrasound creates a microvibration at about 50,000 cycle/sec which is therapeutically beneficial to rejuvenate the trabecular tissue 21.

The ultrasound transducers 136 in FIG. 8 and ultrasound transducers 152 in FIG. 9 serve to image, stimulate and/or rejuvenate the dysfunctional trabecular tissue depending on the ultrasound frequencies used. In accordance with one embodiment, the suitable frequencies for this application are typically in the range of from about 100 kiloHertz (kHz) to about 100 MegaHertz (MHz).

As indicated above, in some embodiments, a suitable cutting edge 150 (FIG. 9) is provided on a selected portion of the tip section 142 with efficacy, as needed or desired, giving due consideration to the goals of providing suitable cutting means on the device 140 for effectively cutting through the trabecular meshwork 21 and/or of achieving one or more of the benefits and advantages as taught or suggested herein.

Figure 10:
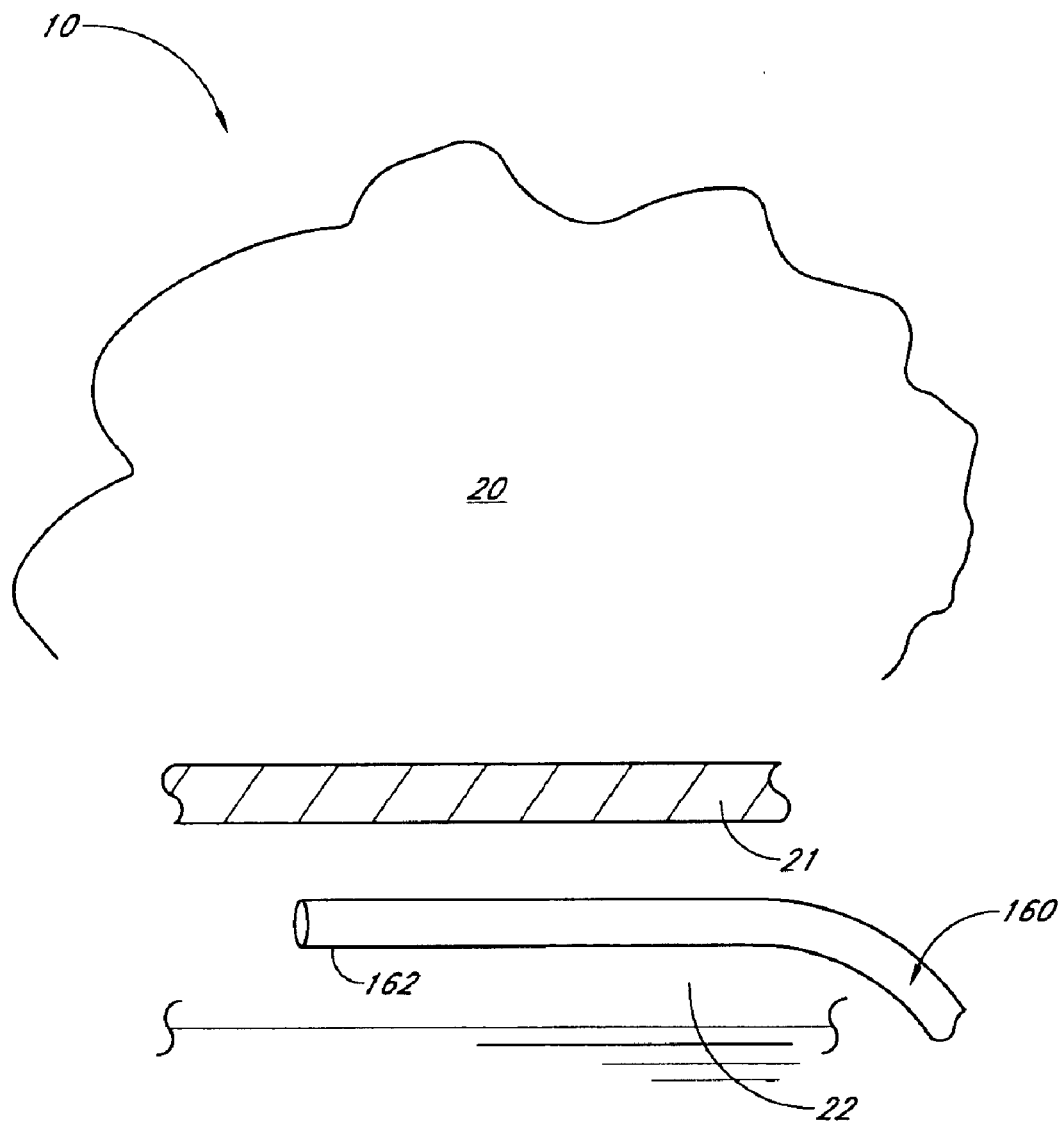
FIG. 10 is a simplified partial view of an eye schematically illustrating the placement and use of a system therein for rejuvenating dysfunctional trabecular meshwork by an ab externo optical energy method and having features and advantages in accordance with one embodiment of the invention.

FIG. 10 is a simplified partial view of an eye 10 generally illustrating the placement and use of a system or fiber optic device 160 therein for rejuvenating dysfunctional trabecular meshwork by an ab externo optical energy method and having features and advantages in accordance with one embodiment. The fiber optic device 160 comprises a tip 162 that is capable of emitting optic signals and receiving the signals. As shown in FIG. 10, the tip 162 is positioned within Schlemm's canal 22.

Referring to FIG. 10, the fiber optic device 160 is deployed to inspect Schlemm's canal 22, collector duct openings, and the adjacent trabecular meshwork 21. The device 160 is useful to inspect the target areas before, during or after a glaucoma treatment of ab interno or ab externo procedures. The optic fiber 160 may also be combined with other catheter embodiments to accomplish multi-function goals. Further, the device 160 can also carry light enabling heating the tip 162 for thermal treatment of Schlemm's canal 22 or the adjacent trabecular meshwork 21 for tissue stimulation/rejuvenating.

More particularly, the fiber optic device 160 (FIG. 10) is capable of analyzing the tissue composition using near infrared Raman spectrum. Wise et al. in U.S. Pat. No. 6,373,567, the entire contents of which are hereby incorporated by reference herein, disclose a dispersive near infrared (IR) Raman spectrometer and a means for tissue chemical identification based on the principles of the intensity of the spectral peak height shift that correlates to chemical concentration.

The optic fiber arrangement as illustrated in FIG. 10 can be used to apply optical coherence tomography (OCT) principles for diagnosing the dysfunctional or diseased Schlemm's canal 22 and/or adjacent trabecular meshwork 21. OCT is a high-resolution imaging modality that can provide in vivo cross-sectional images of tissue structure with a spatial resolution of about 10 to 20 microns (μm). Radhakrishnan et al. reported real-time optical coherence tomography of the anterior segment at 1310 nm (Arch Ophthalmol. 2001;119:1179–1185) from outside of the eye.

Advantageously, the fiber optic arrangement 160 of FIG. 10 enables a high-speed in vivo diagnosis about the dynamic physiological functions of aqueous outflow at about the trabecular meshwork 21 and Schlemm's canal 22 for site-specific determination of the tissue abnormality. In accordance with one embodiment, the suitable wavelengths for this application are typically in the wavelength range of from about 820–840 Nanometers (nm) and about 1300–1320 nm.

Other Features

The device or catheter of the embodiments disclosed herein can be a wide variety of manners. Referring in particular to devices or apparatuses a trabecular meshwork 21 into Schlemm's canal 22 as illustrated in FIGS. 4 Schlemm's canal 22 is typically about less than 400 microns (μm). Accordingly, the devices 42, 140 are dimensioned so that the portion extending into Schlemm's 22 is typically less than about 400 μm. The diameters of the devices 42, 140 are dimensioned typically in the range from about 100 μm to about 300 μm which is roughly the typical range of the thickness of the trabecular meshwork 21. Also referring in particular to catheters, devices or apparatuses inserted into Schlemm's canal 22 as illustrated FIGS. 6–8 and 10, the diameter is dimensioned typically in the range of from about 25 μm to about 200 μm for easy insertion and deployment.

The systems, devices and apparatuses of the exemplary embodiments may be manufactured or fabricated by a wide variety of techniques. These include, without limitation, by molding, extrusion, or other micro-machining techniques, among other suitable techniques.

The trabecular device 42 (FIG. 4), introducer device 72 (FIG. 5), catheter device 92 (6), catheter device 112 (FIG. 7), catheter device 130 (FIG. 8), trabecular device 140 (FIG. 9), fiber optic device 160 (FIG. 10) of the exemplary embodiments preferably comprise a biocompatible material (bio-material) such that inflammation arising due to irritation between the outer surface of the device and the surrounding tissue is minimized. Biocompatible materials which may be used for these devices preferably include, but are not limited to, titanium, titanium alloys, polypropylene, nylon, PMMA (polymethyl medical grade silicone, e.g., Silastic™, available from Dow Corning Midland, Mich.; and polyurethane, e.g., Pellethane™, also available from Dow Corning Corporation.

In other embodiments, the devices of the exemplary embodiments may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other anti-glaucoma drugs, or antibiotics), and the like.

Referring in particular to FIGS. 4 and 9, in an exemplary embodiment of the trabecular meshwork surgery, the patient is placed in the supine position, prepped, draped and anesthetized as necessary. In one embodiment, a small (less than about 1 mm) incision, which may be self-sealing is made through the cornea 12. The corneal incision can be made in a number of ways, for example, by using a micro-knife, among other tools.

Advantageously, the embodiments of the self-trephine device 140 (FIG. 9) allow for a "one-step" procedure to make an incision in the trabecular meshwork and to subsequently treat trabecular meshwork with heating or vibrational energy to stimulate/rejuvenate the tissue of trabecular meshwork leading to a more balanced intraocular pressure (IOP). Desirably, this provides for a faster, safer, and less expensive surgical, procedure.

Ab Externo Insertion of Catheter via Small Puncture

Certain embodiments of such an ab externo insertion of a catheter device via a small puncture are disclosed in copending U.S. application Ser. No. 10/118,578, filed Apr. 8, 2002, entitled GLAUCOMA STENT AND METHODS THEREOF FOR GLAUCOMA TREATMENT, the entire contents of which are hereby incorporated by reference herein.

In the ab externo procedure of FIGS. 6–8 and 10, the respective device 92, 112, 130, 160 is inserted into Schlemm's canal 21 with the aid of an applicator or delivery apparatus that creates a small puncture into the eye 10 from outside. Since the tissue surrounding the trabecular meshwork 21 is optically opaque, an imaging technique, such as ultrasound biomicroscopy (UBM) or a laser imaging technique, is utilized. The imaging provides guidance for the insertion of the device.

Figure 11:
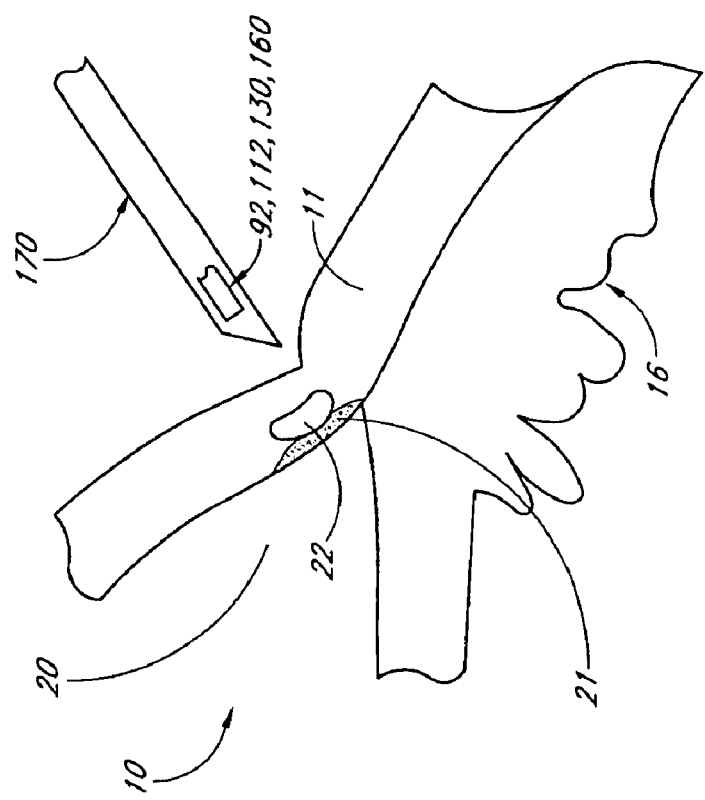
FIG. 11 is a simplified partial view of an eye illustrating the implantation of a medical device using an ab externo procedure having features and advantages in accordance with one embodiment of the invention.

FIG. 11 illustrates the implantation of any of the devices 92, 112, 130, 160 of respective FIGS. 6–8 and 10 using an ab externo procedure having features and advantages in accordance with one embodiment. In the ab externo procedure of FIG. 11, the devices 92, 112, 130, 160 are inserted into Schlemm's canal 21 with the aid of an applicator or delivery apparatus 170 that creates a small puncture into the eye 10 from outside.

Referring to FIG. 11, any of the devices 92, 112, 130, 160 is housed in or held by the applicator 170, and pushed out of the applicator 170 once the applicator tip is in position within the trabecular meshwork 21. Since the tissue surrounding the trabecular meshwork 21 is optically opaque, an imaging technique, such as ultrasound biomicroscopy (UBM) or a laser imaging technique, is utilized. The imaging provides guidance for the insertion of the applicator tip and the deployment of the devices 92, 112, 130, 160. This technique can be used with a large variety of other device embodiments with slight modifications since the trabecular meshwork 21 is punctured from the sclera side rather than the anterior chamber side in the ab externo insertion.

Other Embodiments

Figure 12:
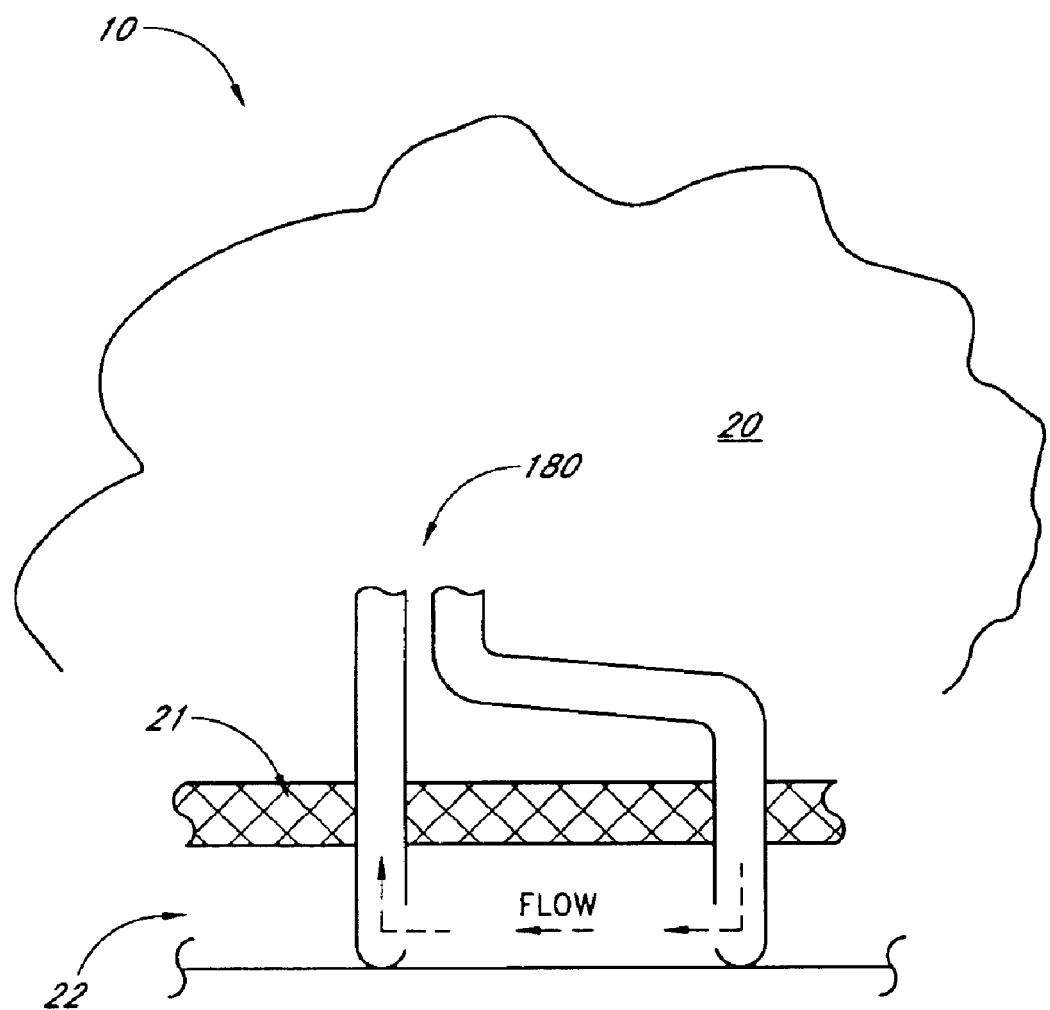
FIG. 12 is a simplified partial view of an eye schematically illustrating the placement and use of a system therein for reversing trabecular outflow to rejuvenate dysfunctional trabecular meshwork utilizing an ab interno procedure and having features and advantages in accordance with one embodiment of the invention.

The embodiment of FIG. 12 enables a completely ab interno procedure that acts upon a limited segment of the Schlemm's canal 22. Both the inflow and outflow portions of the instrument or device 180 are inserted through the trabecular meshwork 21 into Schlemm's canal 22. Since the resistance to flow is greater through the meshwork 21 than through the Schlemm's canal 22, inflow at the point shown will travel around the Schlemm's canal 22 and then exit through the aspiration outflow. This embodiment is particularly well suited to treating or modifying the endothelial lining along a short segment of Schlemm's canal 22.

Figure 13:
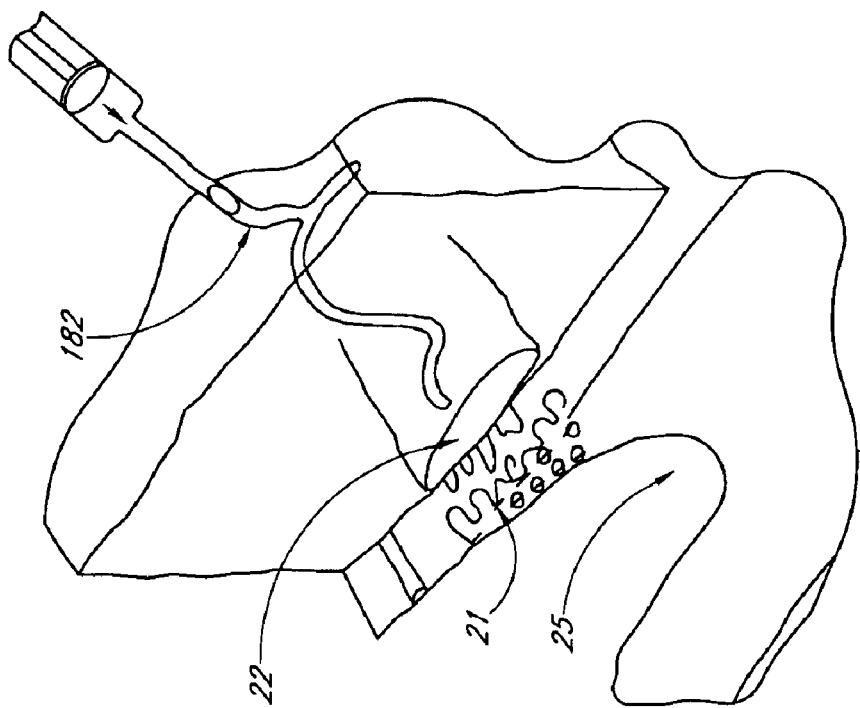
FIG. 13 is a simplified partial view of an eye schematically illustrating an episceral retrograde injection to infuse a liquid into Schlemm's canal and having features and advantages in accordance with one embodiment of the invention.

In the embodiment of FIG. 13, retrograde injection into an episcleral vein 182 is used to infuse a liquid into the Schlemm's canal 22 via a minimally invasive minute puncture on the surface of the eye 10. This provides a means to supply a flushing back flow to flush the trabecular meshwork 21 (could be combined with anterior chamber aspiration if the liquid volume was significant) and to administer drugs or other chemicals directly to the Schlemm's canal 22. Since the flow resistance through the trabecular meshwork 21 is greater than through the Schlemm's canal 22, this retrograde injection would reach a significant fraction of the Schlemm's canal 22. This would also aid in the opening of the Schlemm's canal 22 if it has shrunk as in trabeculectomy patients. This procedure could also be combined with an episcieral ring that is pressed onto the eye to occlude the venous system downstream of the injection point; this would assist in achieving pressures that are high enough to provide back flow through the trabecular meshwork 21.

Figure 14:
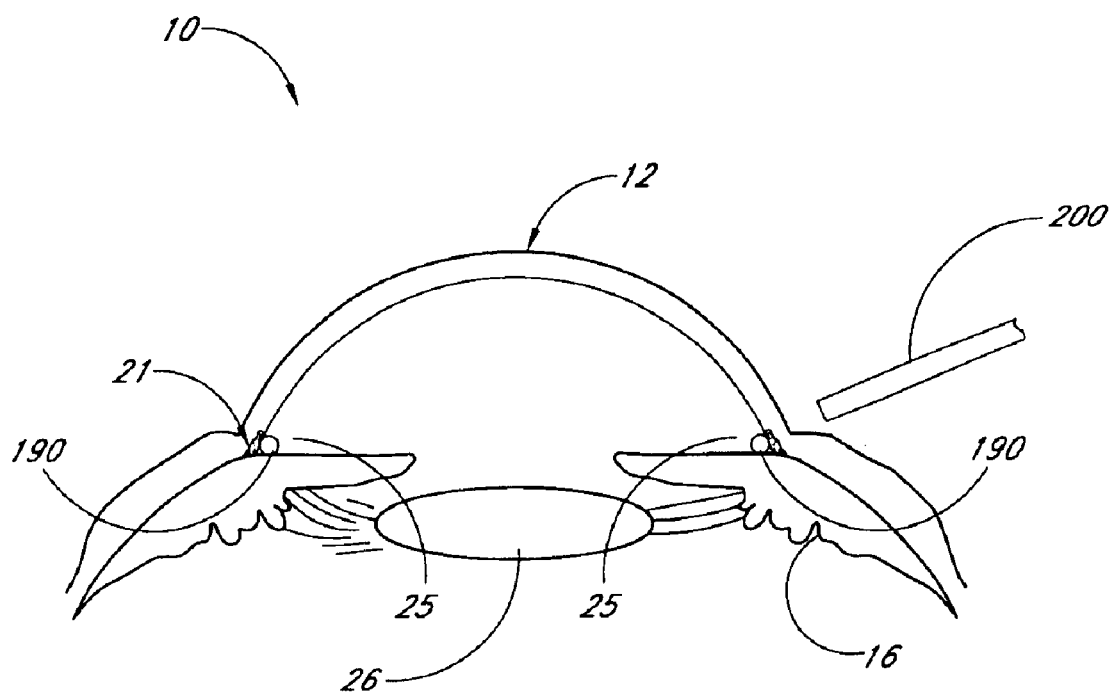
FIG. 14 is a simplified cross-sectional view of an eye illustrating the placement and use of a treatment ring therein and having features and advantages in accordance with one embodiment of the invention.
Figure 15:
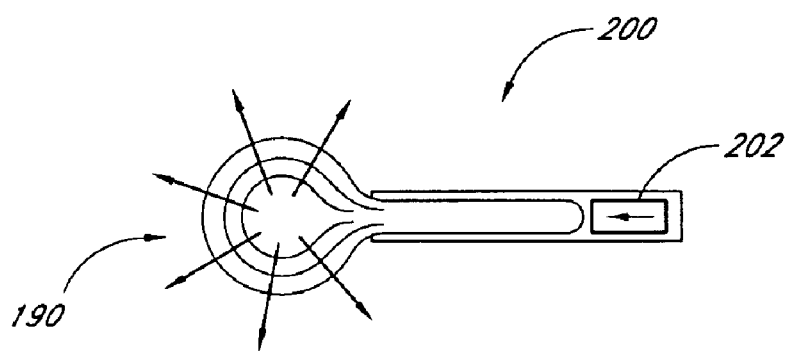
FIG. 15 is a schematic view of an instrument for deploying the treatment ring of FIG. 14 within an eye and having features and advantages in accordance with one embodiment of the invention.

In the embodiment of FIG. 14, a treatment ring or loop 190 is inserted into the anterior angle 25 using a deployment instrument 200 (an embodiment of this instrument is shown in FIG. 15 and utilizes a plunger mechanism 202). The ring 190 when deployed, expands and rests in the angle 25 near the trabecular meshwork 21 and is preferably made from a material that absorbs and slowly releases treatment agents to act on downstream structures (trabecular meshwork, or endothelial lining, or Schlemm's canal, or collector channels, etc.). The advantage is that the drug is delivered directly upstream of where it is needed and naturally flows to the desired downstream sites. This enables lower concentrations of the treatment to be used and targets the desired sites.

Figure 16:
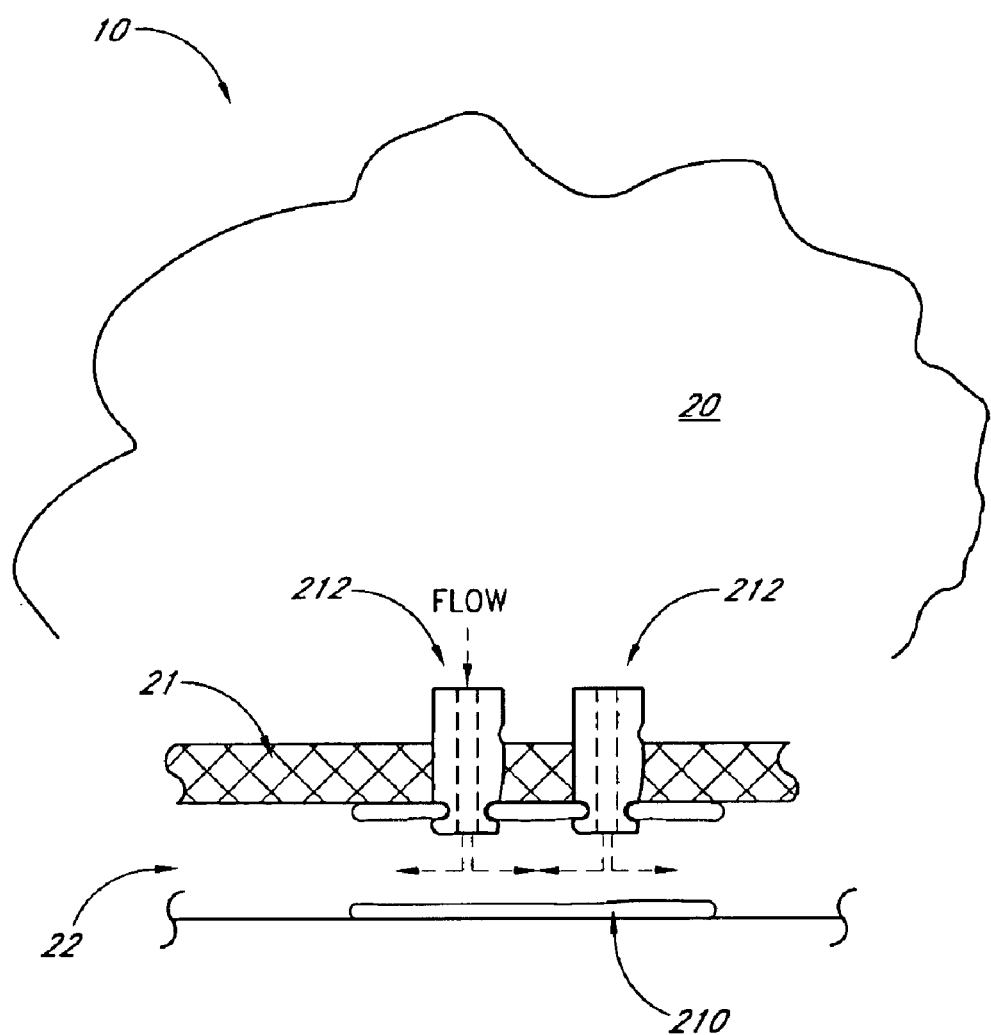
FIG. 16 is a simplified partial view of an eye schematically illustrating the use and placement of a multi-part stent therein and having features and advantages in accordance with one embodiment of the invention.

In the embodiment of FIG. 16, a stent is placed as a series of add-on parts. A tubular (circular, inverted "U" shape, with or without retention barbs, etc.) stent 210 is first inserted into Schlemm's canal 22 to stent open the canal and support the trabecular meshwork 21 for subsequent placement of a snorkel 212 (or multiple snorkels) that provide conduits for flow through the trabecular meshwork 21 into Schlemm's canal 22 and prevent the filling in of the trabecular meshwork 21. The Schlemm's canal stent 210 is inserted either via an ab externo or ab intemo procedure. The snorkel(s) 212 is (are) placed by first making an incision through the trabecular meshwork 21 and the wall of the stent 210; the snorkel(s) 212 is (are) then pushed through the trabecular meshwork 21 until it (they) latches into the Schlemm's canal stent 210. Advantageously, the option to place multiple snorkels provides a means to adjust the outflow resistance of the eye 10 in a series of steps; use of snorkels with a variety of lumen diameters provides finer or coarser flow adjustment. In addition, if a snorkel were to become occluded (and could not be cleared) a replacement snorkel could advantageously be placed adjacent to the inoperative one to restore outflow.

Figure 17A:
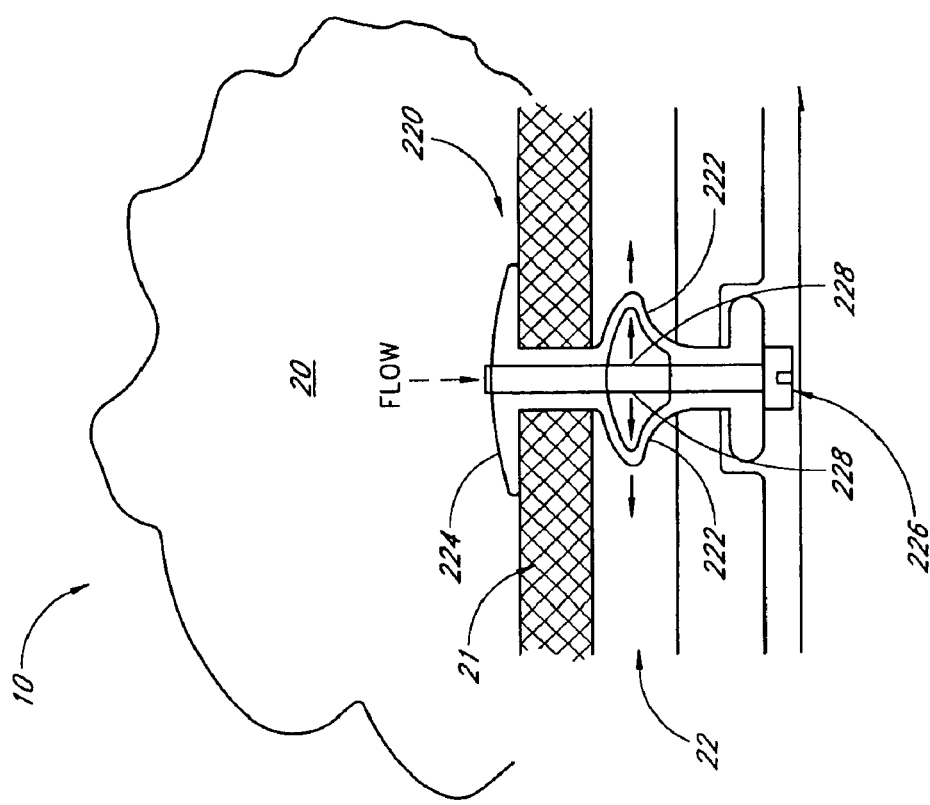
FIG. 17 is a simplified partial view of an eye schematically illustrating the use and placement of a toggle bolt shunt therein and having features and advantages in accordance with one embodiment of the invention.
Figure 17B:
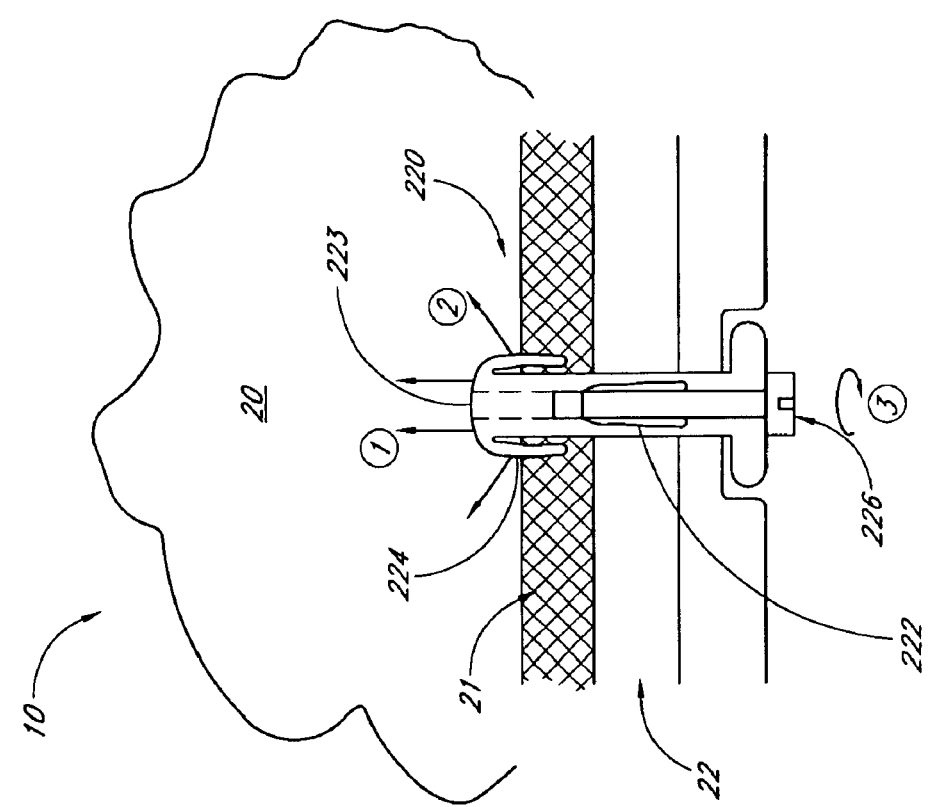

In the embodiment of FIG. 17, a toggle-bolt shunt 220 is shown and relies on the expansion of ribs 222 to support it in Schlemm's canal. The shunt 220 is inserted through the Schlemm's canal 22 and trabecular meshwork 21 via an external procedure (ab externo). Upon passing the tip 223 with flexible wings (or rim) 224 through the trabecular meshwork 21 into the anterior chamber 20, the wings (or rim) 224 flex outward to prevent withdrawal. Turning of a central bolt 226 (or pulling of a central rod as with a pop-rivet) causes the ribs 222 to expand and occupy a portion of the Schlemm's canal 22, providing support for the stent 220. The central bolt or pin 226 is hollow (side ports 228 are included on the bolt for the bolt style) to allow flow from the anterior chamber 20 into Schlemm's canal 22. A modified embodiment, excludes the flexible wings or rim at the tip and relies on adequate length of the tip to protrude above the upper surface of the trabecular meshwork 21. The small external puncture necessary to place this stent could be filled, covered, or glued shut with a suitable bio-glue. With some modification, this toggle-bolt approach could also be accomplished via an ab-interno approach.

Figure 18:
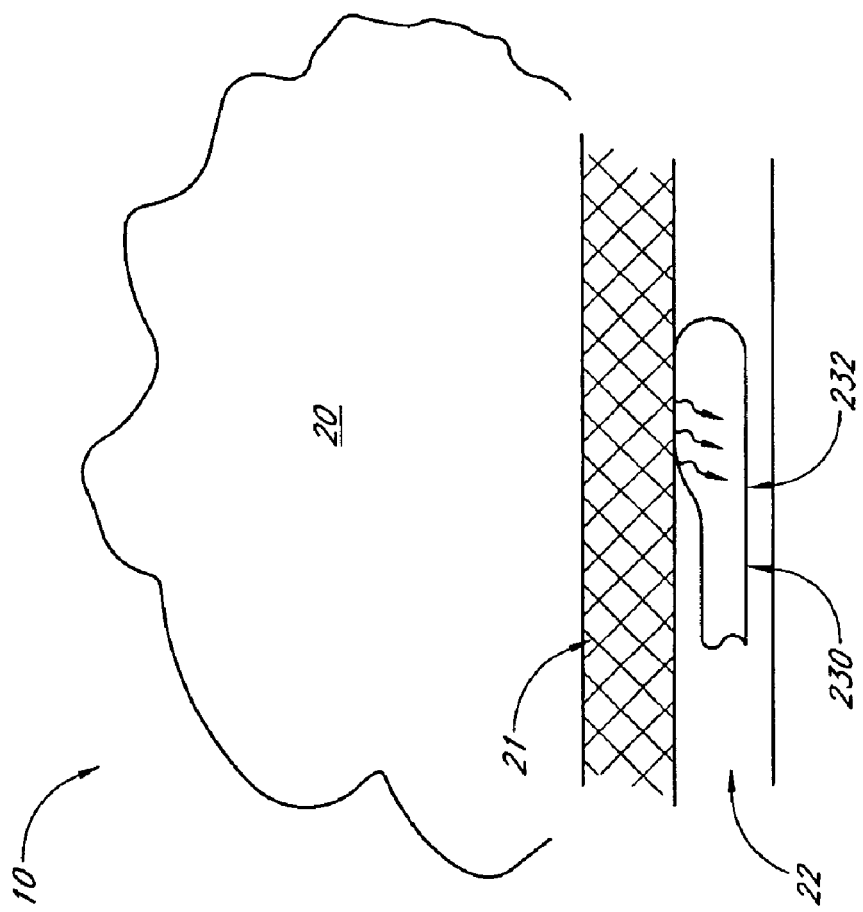
FIG. 18 a simplified partial view of an eye schematically illustrating the use and placement of a thermal catheter device therein and having features and advantages in accordance with one embodiment of the invention.
Figure 19:
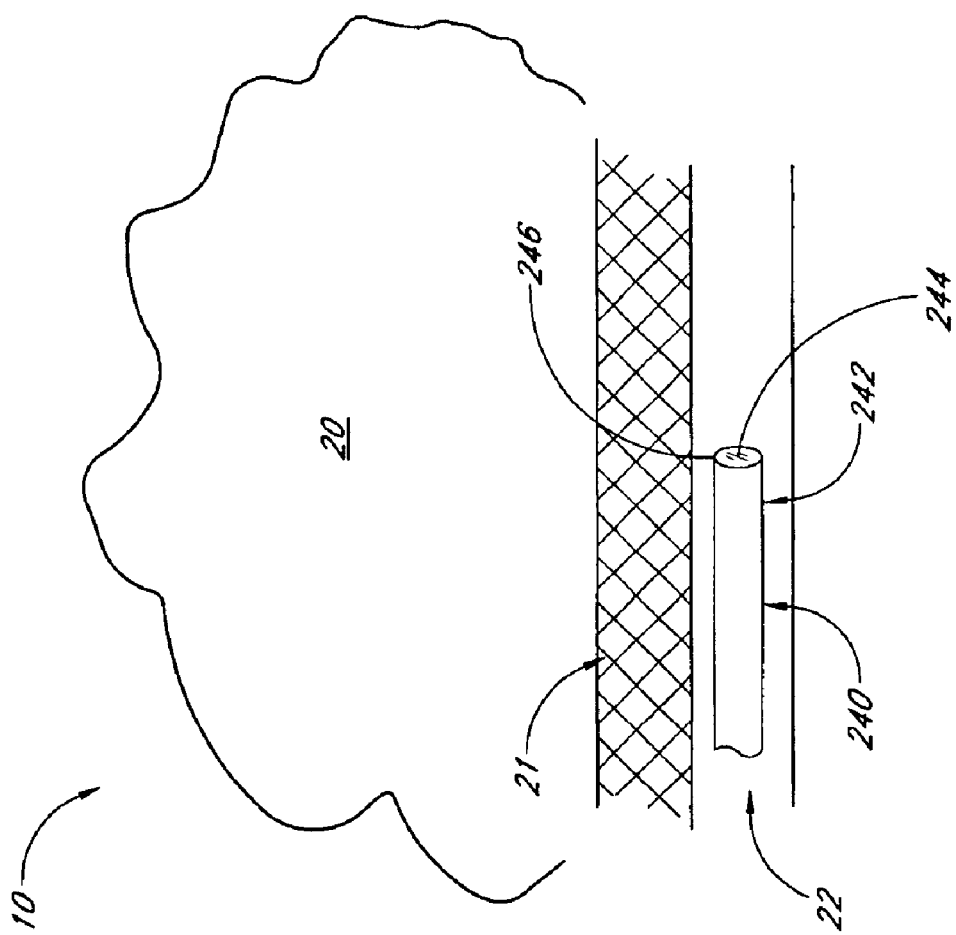
FIG. 19 a simplified partial view of an eye schematically illustrating the use and placement of a vision catheter device

The following embodiments of FIGS. 18 and 19 are tip variations used for catheter based procedures on the Schlemm's canal and trabecular meshwork. In each case, the catheter is guided to the Schlemm's canal from an episcleral vein or portion of the circulatory system further downstream or it is inserted through a puncture in the scleral wall that reaches to the Schlemm's canal. These procedures may be combined to form other multi-function catheters as well, since many of these need not be positioned at the tip of the catheter (they could be at some distance from the tip).

In the embodiment of FIG. 18, a catheter device 230 comprises a thermal catheter tip 232 that is used to either cool or heat the inner wall of Schlemm's canal 22 and the adjacent trabecular meshwork 221. The effected damage to these tissues provides improved flow into the Schlemm's canal 22 by reducing the resistance to outflow through cell death. The induced healing response may also result in healthier tissue.

In the embodiment of FIG. 19, a catheter device 240 comprises a vision catheter tip 242 having a lens 244 at a distal end 246. The device 240 is used to inspect Schlemm's canal 22, collector duct openings, and the adjacent trabecular meshwork 21. This instrument 240 is useful to inspect these areas before, during, or after treatment using the methods described above or other methods. The vision tip 242 may also be combined with other catheter embodiments to accomplish multi-function goals. This catheter could also carry light or other therapeutic radiation to the tip to be used for treatment of the Schlemm's canal or trabecular meshwork.

From the foregoing description, it will be appreciated that a novel approach for the surgical and therapeutic treatment of glaucoma has been disclosed. While the components, techniques and aspects of the invention have been described with a certain degree of particularity, it is manifest that many changes may be made in the specific designs, constructions and methodology herein above described without departing from the spirit and scope of this disclosure.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. A method for treating tissue of trabecular meshwork of an eye by directing a liquid flow through the trabecular meshwork in an opposite direction of a physiological aqueous outflow pathway, the method comprising:

contacting the trabecular meshwork with a distal end of an elongate tubular member;

applying suction to a surface of the trabecular meshwork through a lumen in said elongate tubular member;

flowing fluid into Schlemm's canal of the eye through an end of an elongate body, said end of the elongate body being positioned in Schlemm's canal; and aspirating said fluid from Schlemm's canal through said elongate tubular member.

2. The method of claim 1, wherein the method further comprises providing an inflatable cup balloon mounted at said distal end of said elongate tubular member.

3. The method of claim 1, wherein flowing fluid into Schlemm's canal of the eye comprises infusing a therapeutic liquid through said elongate body for providing said liquid flow through the trabecular meshwork in an opposite direction of the physiological aqueous outflow pathway.

4. The method of claim 3, wherein the therapeutic liquid comprises a pharmaceutical substance, the pharmaceutical substance being a sterile saline.

5. The method of claim 3, wherein the therapeutic liquid comprises a pharmaceutical substance, the pharmaceutical substance being a steroid.

6. The method of claim 3, wherein the therapeutic liquid comprises a pharmaceutical substance, the pharmaceutical substance being a growth factor.

7. The method of claim 3, wherein the therapeutic liquid comprises a pharmaceutical substance, the pharmaceutical substance being an angiogenic inhibitor.

8. The method of claim 3, wherein the therapeutic liquid comprises a pharmaceutical substance, the pharmaceutical substance being Imidazole antiproliferative agents.

9. The method of claim 3, wherein the therapeutic liquid comprises a pharmaceutical substance, the pharmaceutical substance being quinoxoalines.

10. The method of claim 3, wherein the therapeutic liquid comprises a pharmaceutical substance, the pharmaceutical substance being phsophonylmethoxyalkyl nucleotide analogs and related nucleotide analogs.

11. The method of claim 3, wherein the therapeutic liquid comprises a pharmaceutical substance, the pharmaceutical substance being potassium channel blockers.

12. The method of claim 3, wherein the therapeutic liquid comprises a pharmaceutical substance, the pharmaceutical substance being synthetic oligonucleotides.

13. The method of claim 3, wherein the therapeutic liquid comprises a pharmaceutical substance, the pharmaceutical substance being Transforming Growth Factor-beta (TGF-beta).

14. The method of claim 3, wherein the therapeutic liquid comprises a pharmaceutical substance, the pharmaceutical substance being 5-[1-hydroxy-2-[2-(2-methoxyphenoxyl)ethylamino]ethyl]-2-methylbenzenesulfonamide.

15. The method of claim 3, wherein the therapeutic liquid comprises a pharmaceutical substance, the pharmaceutical substance being guanylate cyclase inhibitors.

16. The method of claim 3, wherein the therapeutic liquid comprises a pharmaceutical substance, the pharmaceutical substance being selected from the group consisting of methylene blue, butylated hydroxyanisole, and N-methylhydroxylamine.

17. The method of claim 3, wherein the therapeutic liquid comprises a pharmaceutical substance, the pharmaceutical substance being 2-(4-methylaminobutoxy)diphenylmethane.

18. The method of claim 3, wherein the therapeutic liquid comprises a pharmaceutical substance, the pharmaceutical substance being a combination of apraclonidine and timolol.

19. The method of claim 3, wherein the therapeutic liquid comprises a pharmaceutical substance, the pharmaceutical substance being cloprostenol analogs or fluprostenol analogs.

20. The method of claim 3, wherein the therapeutic liquid comprises a pharmaceutical substance, the pharmaceutical substance being an ophthalmic composition that provides a sustained release of a water-soluble medicament, said water-soluble medicament comprising a crosslinked carboxy-containing polymer, a sugar, and water.

21. The method of claim wherein the therapeutic liquid comprises a pharmaceutical substance, the pharmaceutical substance being a non-corneotoxic serine-threonine kinase inhibitor.

22. The method of claim 3, wherein the therapeutic liquid comprises a pharmaceutical substance, the pharmaceutical substance being a composition of non-steroidal glucocorticoid antagonist.

23. The method of claim 3, wherein the therapeutic liquid comprises a pharmaceutical substance, the pharmaceutical substance being a prostaglandin analog or a derivative thereof.

* * * * *

UNITED STATES PATENT AND TRADEMARK OFFICE
CERTIFICATE OF CORRECTION

PATENT NO. : 7,094,225 B2
APPLICATION NO. : 10/139800
DATED : August 22, 2006
INVENTOR(S) : Tu et al.

It is certified that error appears in the above-identified patent and that said Letters Patent is hereby corrected as shown below:

On Title Page:

On page 1, column 1 (Title), line 2, please delete "OF" and insert --FOR--, therefor.

On page 1, column 2 (Foreign Patent Documents), line 1, delete "AU 200072059 A1 12/2000".

On page 1, column 2 (Foreign Patent Documents), line 5, below "EP 0 898 947 A3 3/1999" please delete "EP 0898 947 A2 3/1999".

On page 1, column 2 (Foreign Patent Documents), line 6, delete "EP 1 114 27 A1".

On page 1, column 2 (Other Publications), line 2, delete "k." and insert --K.--, therefor.

On page 2, column 1 (U.S. Patent Documents), below "6,007,511 A 12/1999 Prywes", please insert --6,033,434 A 3/2000 Borghi--.

On page 2, column 2 (Other Publications), line 7, delete "Opthamology, 199" and insert --Ophthalmology, 1999,--, therefor.

On page 2, column 2 (Other Publications), line 10, delete "Opthalmol." and insert --Ophthalmol,--, therefor.

On page 2, column 2 (Other Publications), line 10, delete "1974." and insert --1974,--, therefor.

On page 2, column 2 (Other Publications), line 16, delete "Congenitial" and insert --Congenital--, therefor.

UNITED STATES PATENT AND TRADEMARK OFFICE
CERTIFICATE OF CORRECTION

PATENT NO. : 7,094,225 B2
APPLICATION NO. : 10/139800
DATED : August 22, 2006
INVENTOR(S) : Tu et al.

It is certified that error appears in the above-identified patent and that said Letters Patent is hereby corrected as shown below:

On Title Page:

On page 2, column 2 (Other Publications), line 21, delete "523 -533." and insert --523-533.--, therefor.

On page 2, column 2 (Other Publications), line 23, delete "Ronald," and insert --Ronald--, therefor.

On page 2, column 2 (Other Publications), line 23, after "Gross," insert --MD,--.

On page 2, column 2 (Other Publications), line 29, delete "Treament" and insert --Treatment--, therefor.

On page 2, column 2 (Other Publications), line 45, delete "Conherence" and insert --Coherence--, therefor.

On page 2, column 2 (Other Publications), line 46, delete "MM," and insert --NM,--, therefor.

On page 3, column 1 (Other Publications), line 2, delete "Iagua," and insert --Iaqua,--, therefor.

On page 3, column 1 (Other Publications), line 4, after "Exp" insert --.--.

On page 3, column 1 (Other Publications), lines 6-32, delete "Phillip C. Jacobi, MD, .......................Oct. 1958, vol. 60, pp.523-533."

On page 3, column 2 (Other Publications), lines 5-31, delete "Detliev Spiegel, MD, .......................entitled: *Expendable/Retractable Stent For Venous and Valvular Annulus Use*".

UNITED STATES PATENT AND TRADEMARK OFFICE
CERTIFICATE OF CORRECTION

| | | |
|---|---|---|
| PATENT NO. | : 7,094,225 B2 | |
| APPLICATION NO. | : 10/139800 | |
| DATED | : August 22, 2006 | |
| INVENTOR(S) | : Tu et al. | |

It is certified that error appears in the above-identified patent and that said Letters Patent is hereby corrected as shown below:

At column 1 (Title), line 2, delete "OF" and insert --FOR--, therefor.

At column 5, line 11 (Approx.), delete "extemo" and insert --externo--, therefor.

At column 5, line 13 (Approx.), delete "intemo" and insert --interno--, therefor.

At column 5, line 62, delete "intemo" and insert --interno--, therefor.

At column 6, line 4, delete "extemo" and insert --externo--, therefor.

At column 6, line 10 (Approx.), delete "extemo" and insert --externo--, therefor.

At column 6, line 16, delete "extemo" and insert --externo--, therefor.

At column 6, line 22, delete "intemo" and insert --interno--, therefor.

At column 6, line 32, delete "extemo" and insert --externo--, therefor.

At column 6, line 38, delete "intemo" and insert --interno--, therefor.

At column 8, lines 44-45, delete "phsophonylmethoxyalkyl" and insert --phosphonylmethoxyalkyl--, therefor.

At column 10, line 9, delete "intemo" and insert --interno--, therefor.

At column 10, line 19, delete "intemo" and insert --interno--, therefor.

At column 10, line 27 (Approx.), delete "intemo" and insert --interno--, therefor.

At column 10, line 65, delete "extemo" and insert --externo--, therefor.

At column 11, line 31 (Approx.), delete "extemo" and insert --externo--, therefor.

UNITED STATES PATENT AND TRADEMARK OFFICE
CERTIFICATE OF CORRECTION

| | | |
|---|---|---|
| PATENT NO. | : 7,094,225 B2 | |
| APPLICATION NO. | : 10/139800 | |
| DATED | : August 22, 2006 | |
| INVENTOR(S) | : Tu et al. | |

It is certified that error appears in the above-identified patent and that said Letters Patent is hereby corrected as shown below:

At column 12, line 40 (Approx.), delete "extemo" and insert --externo--, therefor.

At column 13, line 5, delete "extemo" and insert --externo--, therefor.

At column 14, line 42, delete "extemo" and insert --externo--, therefor.

At column 14, line 52, delete "intemo" and insert --interno--, therefor.

At column 15, line 22, after "can be" insert --dimensioned in--.

At column 15, line 23, after "apparatuses" insert --inserted through--.

At column 15, line 24, after "FIGS. 4" insert --and 9, the depth of--.

At column 15, line 27, after "Schlemm's" insert --canal--.

At column 15, line 42, delete "(6)," and insert --(FIG. 6),--, therefor.

At column 15, line 51, after "(polymethyl" insert --methacrylate),--.

At column 15, line 52, delete "Corning" and insert --Coming Corporation of--, therefor.

At column 16, line 19, delete "surgical," and insert --surgical--, therefor.

At column 16, line 56, delete "sclera" and insert --scleral--, therefor.

At column 16, line 60, delete "intemo" and insert --interno--, therefor.

At column 17, line 17, delete "episciaral" and insert --episcleral--, therefor.

At column 17, line 44, delete "intemo" and insert --interno--, therefor.

UNITED STATES PATENT AND TRADEMARK OFFICE
CERTIFICATE OF CORRECTION

PATENT NO. : 7,094,225 B2
APPLICATION NO. : 10/139800
DATED : August 22, 2006
INVENTOR(S) : Tu et al.

It is certified that error appears in the above-identified patent and that said Letters Patent is hereby corrected as shown below:

At column 19, line 31, in Claim 10, delete "phsophonylmethoxyalkyl" and insert --phosphonylmethoxyalkyl--, therefor.

Signed and Sealed this

Tenth Day of July, 2007

JON W. DUDAS
*Director of the United States Patent and Trademark Office*